United States Patent
Schumacher et al.

(10) Patent No.: US 9,517,226 B2
(45) Date of Patent: Dec. 13, 2016

(54) INHIBITORS FOR TREATING DISEASES CHARACTERIZED BY ATRIAL ENLARGEMENT OR REMODELING

(71) Applicants: Christoph Schumacher, Bettingen (CH); Thomas Holbro, Basel (CH)

(72) Inventors: Christoph Schumacher, Bettingen (CH); Thomas Holbro, Basel (CH)

(73) Assignee: Novartis AG, Basel (CH)

( * ) Notice: Subject to any disclaimer, the term of this patent is extended or adjusted under 35 U.S.C. 154(b) by 0 days.

(21) Appl. No.: 14/422,855

(22) PCT Filed: Aug. 22, 2013

(86) PCT No.: PCT/EP2013/067472
§ 371 (c)(1),
(2) Date: Feb. 20, 2015

(87) PCT Pub. No.: WO2014/029848
PCT Pub. Date: Feb. 27, 2014

(65) Prior Publication Data
US 2015/0190376 A1    Jul. 9, 2015

Related U.S. Application Data

(60) Provisional application No. 61/692,911, filed on Aug. 24, 2012.

(51) Int. Cl.
| | | |
|---|---|---|
| A61K 31/41 | (2006.01) |
| A61K 31/194 | (2006.01) |
| A61K 31/197 | (2006.01) |
| A61K 31/216 | (2006.01) |
| A61K 31/4192 | (2006.01) |

(52) U.S. Cl.
CPC ............ *A61K 31/41* (2013.01); *A61K 31/194* (2013.01); *A61K 31/197* (2013.01); *A61K 31/216* (2013.01); *A61K 31/4192* (2013.01)

(58) Field of Classification Search
None
See application file for complete search history.

(56) References Cited

U.S. PATENT DOCUMENTS 5,217,996 A    6/1993    Ksander

FOREIGN PATENT DOCUMENTS

| WO | 03059345 A1 | 7/2003 |
| WO | 2006086456 A2 | 8/2006 |
| WO | 2007056546 A1 | 5/2007 |
| WO | 2009061713 A1 | 5/2009 |
| WO | 2012027237 A1 | 3/2012 |

OTHER PUBLICATIONS

Aronson, D. et al. Pharmacology and Therapeutics, vol. 135, No. 1, Mar. 23, 2012, pp. 1-17, YP028503167.
Chrysant et al. Drugs of the Future, vol. 36, No. 3, Mar. 1, 2011, pp. 183-190, XP009173432.
Ruilope L.M. et al. The Lancet, vol. 375, No. 9722, Apr. 10, 2010, pp. 1255-1266, XP002676955.
Solomon, S.D. et al. The Lancet, vol. 380, No. 9851, Oct. 1, 2012, pp. 1387-1395, XP055083562.

*Primary Examiner* — Samantha Shterengarts
(74) *Attorney, Agent, or Firm* — David R. Kurlandsky

(57) ABSTRACT

The present invention relates to the NEP inhibitor pro-drug N-(3-carboxy-1-oxopropyl)-(4S)-p-phenylphenylmethyl)-4-amino-(2R)-methylbutanoic acid ethyl ester, or a pharmaceutically acceptable salt thereof; or the NEP inhibitor N-(3-carboxy-1-oxopropyl)-(4S)-p-phenylphenylmethyl)-4-amino-(2R)-methylbutanoic acid, or a pharmaceutically acceptable salt thereof, pro-drug for use in the treatment, prevention or delay of progression of a disease characterized by atrial enlargement and/or remodeling; a method for treatment, prevention or delay of progression of a disease characterized by atrial enlargement and/or remodeling comprising administration of a therapeutically effective amount, or a prophylactically effective amount, of the NEP inhibitor or the NEP inhibitor pro-drug, or a pharmaceutically acceptable salt pro-drug thereof, to a subject, e.g. a human subject, in need of such treatment. The present invention further relates to a pharmaceutical composition or a commercial package comprising the NEP inhibitor or the NEP inhibitor pro-drug, or a pharmaceutically acceptable salt thereof, pro-drug for use in the treatment, prevention or delay of progression of a disease characterized by atrial enlargement and/or remodeling.

10 Claims, 1 Drawing Sheet

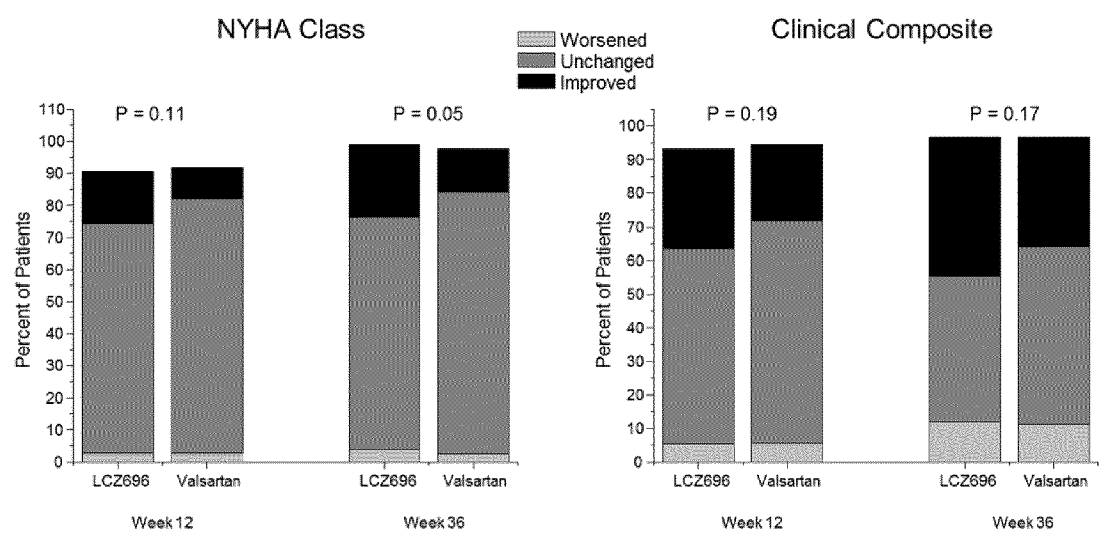

INHIBITORS FOR TREATING DISEASES CHARACTERIZED BY ATRIAL ENLARGEMENT OR REMODELING

The present invention relates to the NEP inhibitor pro-drug N-(3-carboxy-1-oxopropyl)-(4S)-p-phenylphenylmethyl)-4-amino-(2R)-methylbutanoic acid ethyl ester, or a pharmaceutically acceptable salt thereof; or the NEP inhibitor N-(3-carboxy-1-oxopropyl)-(4S)-p-phenylphenylmethyl)-4-amino-(2R)-methylbutanoic acid, or a pharmaceutically acceptable salt thereof, pro-drug for use in the treatment, prevention or delay of progression of a disease characterized by atrial enlargement and/or remodeling; a method for treatment, prevention or delay of progression of a disease characterized by atrial enlargement and/or remodeling comprising administration of a therapeutically effective amount, or a prophylactically effective amount, of the NEP inhibitor or the NEP inhibitor pro-drug, or a pharmaceutically acceptable salt pro-drug thereof, to a subject, e.g. a human subject, in need of such treatment. The present invention further relates to a pharmaceutical composition or a commercial package comprising the NEP inhibitor or the NEP inhibitor pro-drug, or a pharmaceutically acceptable salt thereof, pro-drug for use in the treatment, prevention or delay of progression of a disease characterized by atrial enlargement and/or remodeling.

BACKGROUND OF THE INVENTION

Cardiovascular (CV) disease is the leading cause of death in the western world. The increase in CV disease has not only led to an increase in mortality but an increase in CV morbidity. One of the major forms of CV morbidity is heart failure (HF). HF is a complex clinical syndrome characterized by high mortality, frequent hospitalization, poor quality of life, and a complex therapeutic regimen. In the US alone, HF affects nearly 5 million people and there are an estimated 400,000 newly diagnosed cases annually (American Heart Association, 2006, Heart Disease and Stroke Statistics, 2006 Update, Dallas, Tex.). HF is responsible for more hospitalizations than all forms of cancer combined and is the leading cause of hospitalization in patients older than 65 years of age (American Heart Association, 2006, Heart Disease and Stroke Statistics, 2006 Update, Dallas, Tex.; Adams et al., 2006, J Cardiac Fail, 12(1):10-38.). In-hospital mortality is excessive and readmission is distressingly common, despite advances in pharmacological and device therapies. This need for increased hospitalizations results in enormous direct costs and more is spent annually on the diagnosis and treatment of HF by Medicare than on any other Medicare diagnosis (American Heart Association, 2006, Heart Disease and Stroke Statistics, 2006 Update, Dallas, Tex.; Adams et al., 2006, J Cardiac Fail, 12(1):10-38.). HF is classified as HF with reduced ejection fraction (HF-REF) versus HF with preserved ejection fraction (HF-PEF).

Therapies targeted at improving outcomes in HF-REF have been well studied over the past two decades leading to an improvement in morbidity, mostly in the form of a decrease in re-hospitalization for HF-REF with angiotensin converting enzyme (ACE) inhibitors, angiotensin receptor blockers (ARBs) and β blockers (Cohn et al., 1991, N Engl J Med, 325:303-310; Pfeffer et al., 2003, Lancet, 362:759-766; The CONSENSUS Trial Study Group, 1987, N Engl J Med, 316:1429-1435; The SOLVD Investigators, 1992, N Engl J Med, 327:685-691; The SOLVD Investigators, 1991, N Engl J Med, 325:293-302; Packer et al., 2002, Circulation, 106: 2194-2199).

However, despite the availability of various therapies, HF deaths have continued to rise steadily. This increase has been attributed to the aging of the population and the better survival of underlying diseases, such as for example myocardial infarction, resulting in more incidence of HF as well as the availability of more treatment options which allow HF patients to live longer (American Heart Association, 2006, Heart Disease and Stroke Statistics, 2006 Update, Dallas, Tex.).

It is estimated that 35% to 60% of patients diagnosed with HF have normal or near normal left ventricle ejection fraction (LVEF) (ACC/AHA Guideline, 2005, Circulation, 112:1825-1852). In HF patients with preserved ejection fraction (HF-PEF), there is an impairment of cardiac relaxation resulting in an abnormal ventricular filling (Adams et al., 2006, J Cardiac Fail, 12(1):10-38). Such patients differ from those with HF with reduced ejection fraction (HF-REF) in a number of important ways. Patients with HF-PEF tend to be older and female, and their conditions are more likely to be associated with hypertension rather than with ischemia, and lower percentage of patients have prior myocardial infarction as compared to patients with reduced ejection fraction (Bhatia et al., 2006, N Engl J Med, 355: 260-290).

Pathophysiologic mechanisms that have been implicated in HF-PEF include abnormal diastolic dysfunction with resultant increased ventricular filling pressures, atrial enlargement, increased vascular stiffness, and abnormal systolic function despite relatively preserved ejection fraction.

Left ventricular hypertrophy or concentric remodeling and left atrial enlargement are present in a majority of patients. In addition, left atrial size and left ventricular mass are independently associated with an increased risk of morbidity and mortality. Therefore, the presence of structural remodeling is not only of diagnostic importance but also provide important prognostic insights (Zile et al., 2011, Circulation, 124(23):2491-501). As such a remodeled left atrium indicates increased left ventricular filling pressures that characterize heart failure but also serves as substrate for atrial fibrillation. A treatment that affects or even reduces the remodeling of the cardiac cavities is expected to address the underlying pathophysiology and hence to prevent disease progression.

Atrial Fibrillation (AF) is the most common arrhythmia in patients with Heart Failure (HF); its prevalence increases with the severity of HF, and its occurrence is frequently associated with symptom deterioration and increased morbidity.

Because the renin-angiotensin-aldosterone system (RAAS) is involved in many of the processes associated with HF-PEF, inhibitors of RAS system have been of particular interest as a potential therapeutic intervention for these patients. However, several recently completed large, prospective clinical trials (PEP-CHF, CHARM-Preserved, and I-PRESERVE trials) have not demonstrated a significant benefit of blocking RAAS in improving mortality and morbidity in this population (Cleland et al., 2006, Eur J Heart Failure, 8: 105-110; Yussef et al., 2003, Lancet, 362:777-781; Massie et al., 2008, N Engl J Med., 359(23):2456-67), though these agents have showed favorable effects in patients with a reduced EF.

As a result, to date, there is no proven pharmacologic therapy for the HF-PEF population. Consequently, many of the guidelines for heart failure treatment do not address this group of patients (American Heart Association, 2006, Heart Disease and Stroke Statistics, 2006 Update, Dallas, Tex.;

ESC Guidelines, 2008, Eur Heart J, 29:2388-2442). Rather, treatment options have been focused on treating co-morbidities, such as hypertension or diabetes. Just recently, in 2013, the American Heart Association has added to consider the administer Angiotensin Receptor Blockers (ARBs) to decrease hospitalizations for patients with HF-PEF.

Therefore it would be highly advantageous to provide a new treatment option and indeed providing relief or at least improvement for HF patients, and in particular for HF patients with preserved ejection fraction (HF-PEF).

SUMMARY OF THE INVENTION

Surprisingly, the administration of a NEP (neutral endopeptidase, 3.4.24.11) inhibitor or a pharmaceutically acceptable salt or ester thereof, or pro-drug thereof, in patients with heart failure with preserved ejection fraction (HF-PEF), proved to reduce the left atrial volume, the left atrial volume index (LAVI) and the left atrial dimension.

The present invention thus provides a NEP inhibitor, or a pharmaceutically acceptable salt or ester thereof, or pro-drug thereof, for use in the treatment, prevention or delay of progression of a disease characterized and/or manifested by atrial enlargement and/or remodeling.

There is also provided a NEP inhibitor, or a pharmaceutically acceptable salt or ester thereof, or pro-drug thereof, for use in the reduction of the left atrial volume, the left atrial volume index (LAVI) and/or the left atrial dimension in patients suffering from a disease characterized and/or manifested by atrial enlargement and/or remodeling.

Diseases characterized by atrial enlargement and/or remodeling include, but are not limited to heart failure with preserved ejection fraction (HF-PEF), heart failure with reduced ejection fraction (HF-REF), cardiac dysrhythmias comprising atrial fibrillation, new onset atrial fibrillation and recurrent atrial fibrillation; mitral stenosis and regurgitation, cardiomyopathies, hypertension or pulmonary heart diseases.

In one embodiment, diseases characterized by atrial enlargement and/or remodeling include, but are not limited to, heart failure with preserved ejection fraction (HF-PEF), cardiac dysrhythmias such as atrial fibrillation, new onset atrial fibrillation and recurrent atrial fibrillation, mitral regurgitation, cardiomegalies, cardiomyopathies or pulmonary heart diseases.

There is also provided a NEP inhibitor, or a pharmaceutically acceptable salt or ester thereof, or pro-drug thereof, for use in the improvement, stabilization or delayed worsening in NYHA classification of patients suffering from heart failure.

In one embodiment said patients suffering from heart failure are patients suffering from heart failure with preserved ejection fraction (HF-PEF) or heart failure with reduced ejection fraction (HF-REF). In one embodiment said patients suffering from heart failure are patients suffering from heart failure with preserved ejection fraction (HF-PEF).

In another aspect of the invention, there is provided a pharmaceutical composition, comprising a NEP inhibitor, or a pharmaceutically acceptable salt, or ester thereof, or pro-drug thereof, for use in the treatment, prevention or delay of progression of a disease characterized and/or manifested by atrial enlargement and/or remodeling.

In another aspect, there is also provided a method for treatment, prevention or delay of progression of a disease characterized and/or manifested by atrial enlargement and/or remodeling comprising administration of a therapeutically effective amount, or a prophylactically effective amount, of a NEP inhibitor, or a pharmaceutically acceptable salt or ester thereof, or pro-drug thereof to a subject, e.g. a human subject, in need of such treatment.

There is also provided a method for the reduction of the left atrial volume, the left atrial volume index (LAVI) and/or the left atrial dimension in patients suffering from a disease characterized and/or manifested by atrial enlargement and/or remodeling comprising administration of a therapeutically effective amount of a NEP inhibitor, or a pharmaceutically acceptable salt or ester thereof, or pro-drug thereof, to a subject, e.g. a human, in need of such treatment.

There is also provided a method for the improvement, stabilization or delayed worsening in NYHA classification of patients suffering from heart failure, comprising administration of a therapeutically effective amount of a NEP inhibitor, or a pharmaceutically acceptable salt or ester thereof, or pro-drug thereof, to a subject, e.g. a human, in need of such treatment. In one embodiment said patients suffering from heart failure are patients suffering from heart failure with preserved ejection fraction (HF-PEF) or heart failure with reduced ejection fraction (HF-REF). In one embodiment said patients suffering from heart failure are patients suffering from heart failure with preserved ejection fraction (HF-PEF).

In a further aspect, the present invention provides the use of a NEP inhibitor, or a pharmaceutically acceptable salt or ester thereof, or pro-drug thereof, for the manufacture of a medicament for the treatment, prevention or delay of progression of a disease characterized and/or manifested by atrial enlargement and/or remodeling.

There is also provided the use of a NEP inhibitor, or a pharmaceutically acceptable salt or ester thereof, or pro-drug thereof, for the manufacture of a medicament for one or more of the following purposes:

(a) the reduction of the left atrial volume, the left atrial volume index (LAVI) and/or the left atrial dimension in patients suffering from a disease characterized and/or manifested by atrial enlargement and/or remodeling;

(b) the improvement, stabilization or delayed worsening in NYHA classification of patients suffering from heart failure;

(c) the treatment or prevention of atrial fibrillation or for the prevention of or delay of the time to the new onset of atrial fibrillation in patients suffering from a disease characterized and/or manifested by atrial enlargement and/or remodeling;

(d) the treatment of patients with no history of atrial fibrillation, wherein the NEP inhibitor pro-drug or NEP inhibitor delays the time to the new onset of atrial fibrillation.

Diseases characterized by atrial enlargement and/or remodeling include, but are not limited to heart failure with preserved ejection fraction (HF-PEF), heart failure with reduced ejection fraction (HF-REF), cardiac dysrhythmias comprising atrial fibrillation, new onset atrial fibrillation and recurrent atrial fibrillation; mitral stenosis and regurgitation, cardiomyopathies, hypertension or pulmonary heart diseases.

In one embodiment said patients suffering from heart failure are patients suffering from heart failure with preserved ejection fraction (HF-PEF) or heart failure with reduced ejection fraction (HF-REF). In one embodiment said patients suffering from heart failure are patients suffering from heart failure with preserved ejection fraction (HF-PEF).

The NEP inhibitor pro-drug is preferably N-(3-carboxy-1-oxopropyl)-(4S)-p-phenylphenylmethyl)-4-amino-(2R)- methylbutanoic acid ethyl ester, or a pharmaceutically acceptable salt thereof; and the NEP inhibitor is preferably N-(3-carboxy-1-oxopropyl)-(4S)-p-phenylphenylmethyl)-4-amino-(2R)-methylbutanoic acid, or a pharmaceutically acceptable salt thereof.

In one aspect of the invention, the NEP inhibitor pro-drug or the NEP inhibitor is administered to patients already being treated with an Angiotensin Receptor Blocker, such as valsartan or a pharmaceutically acceptable salt thereof.

In another aspect of the invention, the NEP inhibitor pro-drug or the NEP inhibitor is administered together, concomitantly or sequentially with the Angiotensin Receptor Blocker valsartan or a pharmaceutically acceptable salt thereof.

This invention also provides that the NEP inhibitor pro-drug is administered in the form of LCZ696, i.e. as trisodium [3-((1S,3R)-1-biphenyl-4-ylmethyl-3-ethoxycarbonyl-1-butylcarbamoyl) propionate-(S)-3'-methyl-2'-(pentanoyl{2''-(tetrazol-5-ylate)biphenyl-4'-ylmethyl}amino)butyrate] hemipentahydrate.

BRIEF DESCRIPTION OF THE FIGURES

FIG. 1 shows the changes in NYHA and Clinical Composite assessment of LCZ696 and valsartan treatment groups.

DETAILED DESCRIPTION OF THE INVENTION

Use of a NEP Inhibitor or NEP Inhibitor for Use

The present invention relates to a NEP inhibitor or a pharmaceutically acceptable salt or ester thereof, or pro-drug thereof, preferably the NEP inhibitor pro-drug N-(3-carboxy-1-oxopropyl)-(4S)-p-phenylphenylmethyl)-4-amino-(2R)-methylbutanoic acid ethyl ester or the NEP inhibitor N-(3-carboxy-1-oxopropyl)-(4S)-p-phenylphenylmethyl)-4-amino-(2R)-methylbutanoic acid, or pharmaceutically acceptable salts thereof, for use in the treatment, prevention or delay of progression of a disease characterized and/or manifested by atrial enlargement and/or remodeling.

The present invention also relates to a NEP inhibitor, or a pharmaceutically acceptable salt or ester thereof, or pro-drug thereof, preferably the NEP inhibitor pro-drug N-(3-carboxy-1-oxopropyl)-(4S)-p-phenylphenylmethyl)-4-amino-(2R)-methylbutanoic acid ethyl ester or the NEP inhibitor N-(3-carboxy-1-oxopropyl)-(4S)-p-phenylphenylmethyl)-4-amino-(2R)-methylbutanoic acid, or pharmaceutically acceptable salts thereof, for use in the reduction of the left atrial volume, the left atrial volume index (LAVI) and/or the left atrial dimension in patients suffering from a disease characterized and/or manifested by atrial enlargement and/or remodeling.

The present invention also relates to a NEP inhibitor, or a pharmaceutically acceptable salt or ester thereof, or pro-drug thereof, preferably the NEP inhibitor pro-drug N-(3-carboxy-1-oxopropyl)-(4S)-p-phenylphenylmethyl)-4-amino-(2R)-methylbutanoic acid ethyl ester or the NEP inhibitor N-(3-carboxy-1-oxopropyl)-(4S)-p-phenylphenylmethyl)-4-amino-(2R)-methylbutanoic acid, or pharmaceutically acceptable salts thereof, for use in the treatment, prevention or delay of progression of a disease characterized and/or manifested by atrial enlargement and/or remodeling wherein the treatment, prevention or delay of progression of a disease is characterized by the reduction of the left atrial volume, the left atrial volume index (LAVI) and/or the left atrial dimension in patients suffering from a disease characterized and/or manifested by atrial enlargement and/or remodeling.

Diseases characterized by atrial enlargement and/or remodeling include, but are not limited to heart failure with preserved ejection fraction (HF-PEF), heart failure with reduced ejection fraction (HF-REF), cardiac dysrhythmias comprising atrial fibrillation, new onset atrial fibrillation and recurrent atrial fibrillation; mitral stenosis and regurgitation, cardiomyopathies, hypertension or pulmonary heart diseases.

In one embodiment, diseases characterized by atrial enlargement and/or remodeling include, but are not limited to, heart failure with preserved ejection fraction (HF-PEF), cardiac dysrhythmias such as atrial fibrillation, new onset atrial fibrillation and recurrent atrial fibrillation, mitral regurgitation, cardiomegalies, cardiomyopathies or pulmonary heart diseases.

In one embodiment of the invention the disease characterized and/or manifested by atrial enlargement and/or remodeling is heart failure with preserved ejection fraction (HF-PEF).

In another embodiment of the invention the disease characterized and/or manifested by atrial enlargement and/or remodeling is heart failure with reduced ejection fraction (HF-REF).

In one embodiment of the invention said patient is a warm-blooded animal.

In a further embodiment of the invention said warm-blooded animal is a human.

Furthermore, the present invention relates to a NEP inhibitor, or a pharmaceutically acceptable salt or ester thereof, or pro-drug thereof, preferably the NEP inhibitor pro-drug N-(3-carboxy-1-oxopropyl)-(4S)-p-phenylphenylmethyl)-4-amino-(2R)-methylbutanoic acid ethyl ester or the NEP inhibitor N-(3-carboxy-1-oxopropyl)-(4S)-p-phenylphenylmethyl)-4-amino-(2R)-methylbutanoic acid, or pharmaceutically acceptable salts thereof, for use in the improvement, stabilization or delayed worsening in NYHA classification of patients suffering from heart failure.

In one embodiment patients suffering from heart failure are patients suffering from heart failure with preserved ejection fraction (HF-PEF) or heart failure with reduced ejection fraction (HF-REF). In one embodiment patients suffering from heart failure are patients suffering from heart failure with preserved ejection fraction (HF-PEF).

The New York Heart Association (NYHA) classification grades the severity of heart failure symptoms as one of four functional classes. The NYHA classification is widely used in clinical practice and in research because it provides a standard description of severity that can be used to assess response to treatment and to guide management.

The New York Heart Association functional classification based on severity of symptoms and physical activity:

Class I: No limitation of physical activity. Ordinary physical activity does not cause undue breathlessness, fatigue, or palpitations.

Class II: Slight limitation of physical activity. Comfortable at rest, but ordinary physical activity results in undue breathlessness, fatigue, or palpitations.

Class III: Marked limitation of physical activity. Comfortable at rest, but less than ordinary physical activity results in undue breathlessness, fatigue, or palpitations.

Class IV: Unable to carry on any physical activity without discomfort. Symptoms at rest can be present. If any physical activity is undertaken, discomfort is increased.

In one embodiment of the invention the NEP inhibitor, or a pharmaceutically acceptable salt or ester thereof, or pro-drug thereof, preferably the NEP inhibitor pro-drug N-(3-carboxy-1-oxopropyl)-(4S)-p-phenylphenylmethyl)-4-amino-(2R)-methylbutanoic acid ethyl ester or the NEP inhibitor N-(3-carboxy-1-oxopropyl)-(4S)-p-phenylphenylmethyl)-4-amino-(2R)-methylbutanoic acid, or pharmaceutically acceptable salts thereof, is for the treatment or prevention of atrial fibrillation or for the prevention of or for delaying the time until new onset of atrial fibrillation.

In a further embodiment, the NEP inhibitor, or a pharmaceutically acceptable salt or ester thereof, or pro-drug thereof, preferably the NEP inhibitor pro-drug N-(3-carboxy-1-oxopropyl)-(4S)-p-phenylphenylmethyl)-4-amino-(2R)-methylbutanoic acid ethyl ester or the NEP inhibitor N-(3-carboxy-1-oxopropyl)-(4S)-p-phenylphenylmethyl)-4-amino-(2R)-methylbutanoic acid, or pharmaceutically acceptable salts thereof, is for the treatment or prevention of atrial fibrillation or for the prevention of or for delaying the time until new onset of atrial fibrillation in patients suffering from a disease characterized and/or manifested by atrial enlargement and/or remodeling.

In another embodiment, the NEP inhibitor, or a pharmaceutically acceptable salt or ester thereof, or pro-drug thereof, preferably the NEP inhibitor pro-drug N-(3-carboxy-1-oxopropyl)-(4S)-p-phenylphenylmethyl)-4-amino-(2R)-methylbutanoic acid ethyl ester or the NEP inhibitor N-(3-carboxy-1-oxopropyl)-(4S)-p-phenylphenylmethyl)-4-amino-(2R)-methylbutanoic acid, or pharmaceutically acceptable salts thereof, is for the treatment or prevention of atrial fibrillation or for the prevention of or for delaying the time until new onset of atrial fibrillation in patients suffering from heart failure. In one embodiment patients suffering from heart failure are patients suffering from heart failure with preserved ejection fraction (HF-PEF) or heart failure with reduced ejection fraction (HF-REF). In one embodiment patients suffering from heart failure are patients suffering from heart failure with preserved ejection fraction (HF-PEF).

In one embodiment of the invention the NEP inhibitor, or a pharmaceutically acceptable salt or ester thereof, or pro-drug thereof, preferably the NEP inhibitor pro-drug N-(3-carboxy-1-oxopropyl)-(4S)-p-phenylphenylmethyl)-4-amino-(2R)-methylbutanoic acid ethyl ester or the NEP inhibitor N-(3-carboxy-1-oxopropyl)-(4S)-p-phenylphenylmethyl)-4-amino-(2R)-methylbutanoic acid, or pharmaceutically acceptable salts thereof, is for the treatment of patients suffering from heart failure with preserved ejection fraction (HF-PEF) with no history of atrial fibrillation.

In one embodiment of the invention the NEP inhibitor, or a pharmaceutically acceptable salt or ester thereof, or pro-drug thereof, preferably the NEP inhibitor pro-drug N-(3-carboxy-1-oxopropyl)-(4S)-p-phenylphenylmethyl)-4-amino-(2R)-methylbutanoic acid ethyl ester or the NEP inhibitor N-(3-carboxy-1-oxopropyl)-(4S)-p-phenylphenylmethyl)-4-amino-(2R)-methylbutanoic acid, or pharmaceutically acceptable salts thereof, is for the treatment of patients suffering from heart failure with preserved ejection fraction (HF-PEF) with no history of atrial fibrillation, wherein the NEP inhibitor pro-drug or NEP inhibitor prevents or delays the time to the new onset of atrial fibrillation.

In one embodiment thereof, the NEP inhibitor, or a pharmaceutically acceptable salt or ester thereof, or pro-drug thereof, preferably the NEP inhibitor pro-drug N-(3-carboxy-1-oxopropyl)-(4S)-p-phenylphenylmethyl)-4-amino-(2R)-methylbutanoic acid ethyl ester or the NEP inhibitor N-(3-carboxy-1-oxopropyl)-(4S)-p-phenylphenylmethyl)-4-amino-(2R)-methylbutanoic acid, or pharmaceutically acceptable salts thereof, is superior to valsartan alone and/or enalapril alone in delaying the time to the new onset of atrial fibrillation.

In one embodiment of the invention, the NEP inhibitor, or a pharmaceutically acceptable salt or ester thereof, or pro-drug thereof, preferably the NEP inhibitor pro-drug N-(3-carboxy-1-oxopropyl)-(4S)-p-phenylphenylmethyl)-4-amino-(2R)-methylbutanoic acid ethyl ester or the NEP inhibitor N-(3-carboxy-1-oxopropyl)-(4S)-p-phenylphenylmethyl)-4-amino-(2R)-methylbutanoic acid, or pharmaceutically acceptable salts thereof, is for use of reducing the level of plasma NT-proBNP in patients suffering from a disease characterized and/or manifested by atrial enlargement and/or remodeling, such as heart failure, in particular heart failure with preserved ejection fraction.

In another embodiment of the invention, the NEP inhibitor, or a pharmaceutically acceptable salt or ester thereof, or pro-drug thereof, preferably the NEP inhibitor pro-drug N-(3-carboxy-1-oxopropyl)-(4S)-p-phenylphenylmethyl)-4-amino-(2R)-methylbutanoic acid ethyl ester or the NEP inhibitor N-(3-carboxy-1-oxopropyl)-(4S)-p-phenylphenylmethyl)-4-amino-(2R)-methylbutanoic acid, or pharmaceutically acceptable salts thereof,—when administered or used in the context of the invention—leads to a sustained reduction in plasma NT-proBNP concentration.

In the context of the present invention and all the aforementioned embodiments, the NEP inhibitor, or a pharmaceutically acceptable salt or ester thereof, or pro-drug thereof, preferably the NEP inhibitor pro-drug N-(3-carboxy-1-oxopropyl)-(4S)-p-phenylphenylmethyl)-4-amino-(2R)-methylbutanoic acid ethyl ester or the NEP inhibitor N-(3-carboxy-1-oxopropyl)-(4S)-p-phenylphenylmethyl)-4-amino-(2R)-methylbutanoic acid, or pharmaceutically acceptable salts thereof, can in addition be used for the improvement, stabilization or delayed worsening in NYHA classification of patients suffering from heart failure. In one embodiment said patients suffering from heart failure are patients suffering from heart failure with preserved ejection fraction (HF-PEF) or heart failure with reduced ejection fraction (HF-REF). In one embodiment said patients suffering from heart failure are patients suffering from heart failure with preserved ejection fraction (HF-PEF).

Definitions

Throughout this specification and in the claims that follow, the following terms are defined with the following meanings, unless explicitly stated otherwise.

The term "prevention" refers to prophylactic administration to a healthy subject to prevent the development of the conditions mentioned herein. Moreover, the term "prevention" means prophylactic administration to patients being in a pre-stage of the conditions to be treated.

The term "delay of progression", as used herein, refers to administration to patients being in a pre-stage of the condition to be treated in which patients with a pre-form of the corresponding condition is diagnosed.

The term "treatment" is understood the management and care of a patient for the purpose of combating the disease, condition or disorder.

The term "therapeutically effective amount" refers to an amount of a drug or a therapeutic agent that will elicit the desired biological and/or medical response of a tissue, system or an animal (including man) that is being sought by a researcher or clinician.

The terms "warm-blooded animal or patient" include, but are not limited to, humans, dogs, cats, horses, pigs, cows, monkeys, rabbits and mice. The preferred mammals are humans.

The terms "administration of" and or "administering a" compound should be understood to mean providing a compound of the invention or a pharmaceutically acceptable salt or ester thereof, or a pro-drug thereof to a subject in need of treatment. The administration of the composition of the present invention in order to practice the present methods of therapy is carried out by administering a therapeutically effective amount of the compounds in the composition to a subject in need of such treatment or prophylaxis. The need for a prophylactic administration according to the methods of the present invention is determined via the use of well-known risk factors. The effective amount of an individual compound is determined, in the final analysis, by the physician in charge of the case, but depends on factors such as the exact disease to be treated, the severity of the disease and other diseases or conditions from which the patient suffers, the chosen route of administration, other drugs and treatments which the patient may concomitantly require, and other factors in the physician's judgment.

The term "prophylactically effective amount" as used herein means the amount of the active compounds in the composition that will elicit the biological or medical response in a tissue, system, subject, or human that is being sought by the researcher, veterinarian, medical doctor or other clinician, to prevent the onset of a disease characterized and/or manifested by atrial enlargement and/or remodeling.

The term "pharmaceutically acceptable", as used herein, refers to those compounds, materials, compositions and/or dosage forms, which are, within the scope of sound medical judgment, suitable for contact with the tissues of mammals, especially humans, without excessive toxicity, irritation, allergic response and other problem complications commensurate with a reasonable benefit/risk ratio.

Neutral Endopeptidase

Neutral endopeptidase (EC 3.4.24.11; enkephalinase; atriopeptidase; NEP; Biochem. J., 241, p. 237-247, 1987) is a zinc-containing metalloprotease that cleaves a variety of peptide substrates on the amino terminal side of aromatic amino acids. Substrates for this enzyme include, but are not limited to, atrial natriuretic factors (ANF, also known as ANP), brain natriuretic peptide (BNP), met and leu enkephalin, bradykinin, neurokinin A, and substance P.

ANPs are a family of vasodilator, diuretic and antihypertensive peptides which have been the subject of many reports in the literature, e.g., Annu. Rev. Pharm. Tox., 29, 23-54, 1989. One form, ANF 99-126, is a circulating peptide hormone which is released from the heart during conditions of cardiac distension. The function of ANF is to maintain salt and water homeostasis as well as to regulate blood pressure. ANF is rapidly inactivated in the circulation by at least two processes: by a receptor-mediated clearance as reported in Am. J. Physiol., 256, R469-R475, 1989, and by an enzymatic inactivation via NEP as described in Biochem. J., 243, 183-187, 1987. It has been previously demonstrated that inhibitors of NEP potentiate the hypotensive, diuretic, natriuretic and plasma ANF responses to pharmacological injection of ANF in experimental animals. The potentiation of ANF by two specific NEP inhibitors is reported by Sybertz et al. in J. Pharmacol. Exp. Ther 250, 2, 624-631, 1989, and in Hypertension, 15, 2, 152-161, 1990, while the potentiation of ANF by NEP—A—in general was disclosed in U.S. Pat. No. 4,749,688. In U.S. Pat. No. 4,740,499 Olins disclosed the use of thiorphan and kelatorphan to potentiate atrial peptides. Moreover, NEP inhibitors lower blood pressure and exert ANF-like effects such as diuresis and increased cyclic guanosine 3',5'-monophosphate (cGMP) excretion in some forms of experimental hypertension. The antihypertensive action of NEP inhibitors is mediated through ANF because antibodies to ANF will neutralize the reduction in blood pressure.

The in vitro inhibition of neutral endopeptidase (NEP) 3.4.24.11 can be, for example, determined as follows: Neutral endopeptidase 3.4.24.11 activity can be determined by the hydrolysis of the substrate glutaryl-Ala-Ala-Phe-2-naphthylamide (GAAP) using a modified procedure of Orlowski and Wilk (1981). The incubation mixture (total volume 125 μl) contains 4.2 μg of protein (rat kidney cortex membranes prepared by method of Maeda et al, 1983), 50 mM tris buffer, pH 7.4 at 25 C.°, 500 μM substrate (final concentration), and leucine aminopeptidase M (2.5 μg). The mixture is incubated for 10 minutes at 25 C.° and 100 μl of fast garnet (250 μg fast garnet/ml of 10% Tween 20 in 1M sodium acetate, pH 4.2) is added. Enzyme activity is measured spectrophotometrically at 540 nm. One unit of NEP 24.11 activity is defined as 1 nmol of 2-naphthylamine released per minute at 25 C.° at pH 7.4. IC 50 values are determined, i.e. the concentration of test compound required for 50% inhibition of the release of 2-naphthylamine.

Neutral endopeptidase activity can be also determined using ANF as a substrate. Atrial natriuretic factor degrading activity is determined by measuring the disappearance of rat-ANF (r-ANF) using a 3 minute reverse phase-HPLC separation. An aliquot of the enzyme in 50 mM Tris HCl buffer, pH 7.4, is preincubated at 37 C.° for 2 minutes and the reaction is initiated by the addition of 4 nmol of r-ANF in a total volume of 50 μl. The reaction is terminated after 4 minutes with the addition of 30 μl of 0.27% trifluoroacetic acid (TFA). Forty microliters of the mixture is injected into a reverse phase-HPLC and analyzed using a C4 cartridge in a 3 minute, isocratic separation. Twenty-three percent of buffer B (0.1% TFA in 80% acetonitrile) is used. Buffer A is 0.1% TFA in water. One unit of activity is defined as the hydrolysis of 1 nmol of r-ANF per minute at 37° C. at pH 7.4. IC 50 values are determined, i.e. the concentration of test compound required for 50% inhibition of the hydrolysis of ANF.

The test compound can be dissolved, for example, in dimethyl sulfoxide or 0.25M sodium bicarbonate solution, and the solution is diluted with pH 7.4 buffer to the desired concentration.

NEP Inhibitor Pro-Drugs and NEP Inhibitors

The methods and compositions of the present invention comprise a NEP inhibitor, or a pharmaceutically acceptable salt or ester thereof or pro-drug thereof. The NEP inhibitor useful in the compositions of the present invention may be any NEP inhibitor known in the art.

A suitable NEP inhibitor which may be employed in the present invention is, e.g., a compound of the formula (I)

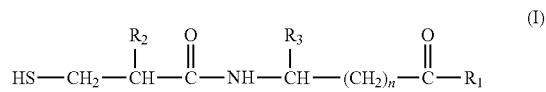

wherein
$R_2$ is $C_1$-$C_7$ alkyl, trifluoromethyl, optionally substituted phenyl or —$(CH_2)_{1-4}$-(optionally substituted phenyl);

R$_3$ is hydrogen, C$_1$-C$_7$alkyl, optionally substituted phenyl, —(CH$_2$)$_{1-4}$-(optionally substituted phenyl);

R$_1$ is hydroxy, C$_1$-C$_7$ alkoxy or NH$_2$;

n is an integer from 1 to 15;

or pharmaceutically acceptable salts thereof.

The term "optionally substituted phenyl" refers to a phenyl group which may optionally be substituted with a substituent selected from C$_1$-C$_4$ alkyl, C$_1$-C$_4$ alkoxy, C$_1$-C$_4$ alkylthio, hydroxy, Cl, Br, or F.

Preferred selective NEP inhibitors of formula (I) include compounds wherein:

R$_2$ is benzyl;

R$_3$ is hydrogen;

n is an integer from 1 to 9;

R$_1$ is hydroxy;

or pharmaceutically acceptable salts thereof.

Further preferred is a selective NEP inhibitor of formula (I) which is reported in the literature as SQ 28,603 wherein:

R$_2$ is benzyl;

R$_3$ is hydrogen;

n is one; and

R$_1$ is hydroxy.

The preparation of selective NEP inhibitors of formula (I) wherein R$_2$ is other than trifluoromethyl is disclosed by Delaney et al. in U.S. Pat. No. 4,722,810. The preparation of selective NEP inhibitors of formula (I) wherein R$_2$ is trifluoromethyl is disclosed by Delaney et al. in U.S. Pat. No. 5,223,516.

Further NEP inhibitors within the scope of the present invention include compounds disclosed in U.S. Pat. No. 4,610,816, herein incorporated by reference, including in particular N-[N-[1 (S)-carboxyl-3-phenylproplyl]-(S)-phenylalanyl]-(S)-isoserine and N-[N-[((1S)-carboxy-2-phenyl)ethyl]-(S)-phenylalanyl]-β-alanine; compounds disclosed in U.S. Pat. No. 4,929,641, in particular N-[2(S)-mercaptomethyl-3-(2-methylphenyl)-propionyl]-methionine; SQ 28,603 (N-[2-(mercaptomethyl)-1-oxo-3-phenylpropyl]-β-alanine), disclosed in South African Patent Application 84/0670; UK 69578 (cis-4-[[[1-[2-carboxy-3-(2-methoxyethoxy)-propyl]-cyclopentyl]carbonyl]amino]-cyclohexanecarboxylic acid) and its active enantiomer(s); thiorphan and its enantiomers; retro-thiorphan; phosphoramidon; and SQ 29,072 (7-[[2-(mercaptomethyl)-1-oxo-3-phenylpropyl]amino]-heptanoic acid).

NEP inhibitors within the scope of the present invention also include the compounds disclosed in U.S. Pat. No. 5,217,996, particularly, N-(3-carboxy-1-oxopropyl)-(4S)-p-phenylphenylmethyl)-4-amino-(2R)-methylbutanoic acid ethyl ester and N-(3-carboxy-1-oxopropyl)-(4S)-p-phenylphenylmethyl)-4-amino-(2R)-methylbutanoic acid, or in each case, a pharmaceutically acceptable salt thereof; the compounds disclosed in EP 00342850, particularly (S)-cis-4-[1-[2-(5-indanyloxycarbonyl)-3-(2-methoxyethoxy)propyl]-1-cyclopentanecarboxamido]-1-cyclohexanecarboxylic acid; the compounds disclosed in GB 02218983, particularly 3-(1-[6-endo-hydroxymethylbicyclo[2,2,1]heptane-2-exo-carbamoyl]-cyclopentyl)-2-(2-methoxyethyl)propanoic acid; the compounds disclosed in WO 92/14706, particularly N-(1-(3-(N-t-butoxycarbonyl-(S)-prolylamino)-2(S)-t-butoxy -carbonylpropylycyclopentanecarbonyl)-O-benzyl-(S)-serine methyl ester; the compounds disclosed in EP 00343911; the compounds disclosed in JP 06234754; the compounds disclosed in EP 00361365, particularly 4-[[2-(mercaptomethyl)-1-oxo-3-phenylpropyl]amino]benzoic acid; the compounds disclosed in WO 90/09374, particularly 3-[1-(cis-4-carboxycarbonyl-cis-3-butylcyclohexyl-r-1-carboamoyl)cyclopentyl]-2S-(2-methoxyethoxymethyl)propanoic acid; the compounds disclosed in JP 07157459, particularly N-((2S)-2-(4-biphenylmethyl)-4-carboxy-5-phenoxyvaleryl)glycine; the compounds disclosed in WO 94/15908 particularly N-(1-(N-hydroxycarbamoylmethyl)-1-cyclopentanecarbonyl)-L-phenylalanine; the compounds disclosed in U.S. Pat. No. 5,273,990 particularly (S)-(2-biphenyl-4-yl)-1-(1H-tetrazol-5-yl)ethylamino)methylphosphonic acid; the compounds disclosed in U.S. Pat. No. 5,294,632 particularly (S)-5-(N-(2-(phosphonomethylamino)-3-(4-biphenyl)propionyl)-2-aminoethyl)tetrazole; the compounds disclosed in U.S. Pat. No. 5,250,522, particularly β-alanine, 3-[1,1'-biphenyl]-4-yl-N-[diphenoxyphosphinyl)methyl]-L-alanyl; the compounds disclosed in EP 00636621, particularly N-(2-carboxy-4-thienyl)-3-mercapto-2-benzylpropanamide; the compounds disclosed in WO 93/09101, particularly 2-(2-mercaptomethyl-3-phenyl-propionamido)thiazol-4-ylcarboxylic acid; the compounds disclosed in EP 00590442 particularly ((L)-(1-((2,2-dimethyl-1,3-dioxolan-4-yl)-methoxy)carbonyl)-2-phenyl-ethyl)-L-phenylalanyl)-3-alanine, N-[N-[(L)-[1-[(2,2-dimethyl-1,3-dioxolan-4-yl)-methoxy]carbonyl]-2-phenylethyl]-L-phenylalanyl]-(R)-alanine, N-[N-[(L)-1-carboxy-2-phenylethyl]-L-phenylalanyl]-(R)-alanine, N-[2-acetylthiomethyl-3-(2-methyl-phenyl)-propionyl]-methionine ethyl ester, N-[2-mercaptomethyl-3-(2-methylphenyl)propioyl]-methionine, N-[2(S)-mercaptomethyl-3-(2-methylphenyl)propanoyl]-(S)-isoserine, N-(S)-[3-mercapto-2-(2-methylphenyl)propionyl]-(S)-2-methoxy-(R)-alanine, N-[1-[[1(S)-benzyloxycarbonyl-3-phenylpropyl]amino]cyclopentylcarbonyl]-(S)-isoserine, N-[1-[[1(S)-carbonyl-3-phenylpropy]amino]-cyclopentylcarbonyl]-(S)-isoserine, 1,1'-[dithiobis-[2(S)-(2-methylbenzyl)-1-oxo-3,1-propanediyl]]-bis-(S)-isoserine, 1,1'-[dithiobis-[2(S)-(2-methylbenzyl)-1-oxo-3,1-propanediyl]]-bis-(S)-methionine, N-(3-phenyl-2-(mercaptomethyl)-propionyl)-(S)-4-(methylmercapto)methionine, N-[2-acetylthiomethyl-3-phenyl-propionyl]-3-aminobenzoic acid, N-[2-mercaptomethyl-3-phenyl-propionyl]-3-aminobenzoic acid, N-[1-(2-carboxy-4-phenylbutyl)-cyclopentanecarbonyl]-(S)-isoserine, N-[1-(acetylthiomethyl)-cyclopentane-carbonyl]-(S)-methionine ethyl ester, 3(S)-[2-{acetylthiomethyl}-3-phenyl-propionyl]amimo-e-caprolactam; and the compounds disclosed in WO 93/10773, particularly, N-(2-acetylthiomethyl-3-(2-methylphenyl)propionyl)-methionine ethyl ester.

Also suitable for use are any pro-drug forms of the above-listed NEP inhibitors, e.g., compounds in which one or more carboxylic acid groups are esterified.

Especially suitable NEP inhibitors include N-(3-carboxy-1-oxopropyl)-(4S)-p-phenylphenylmethyl)-4-amino-(2R)-methylbutanoic acid ethyl ester and N-(3-carboxy-1-oxopropyl)-(4S)-p-phenylphenylmethyl)-4-amino-(2R)-methylbutanoic acid of the formulae

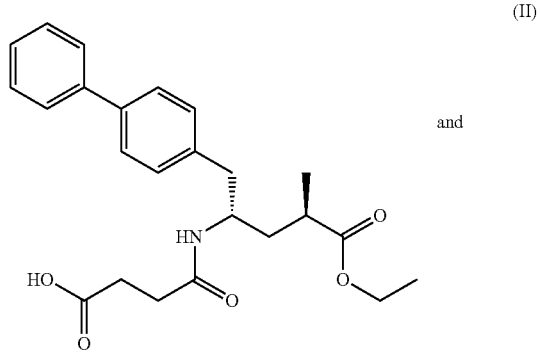

(II)

and

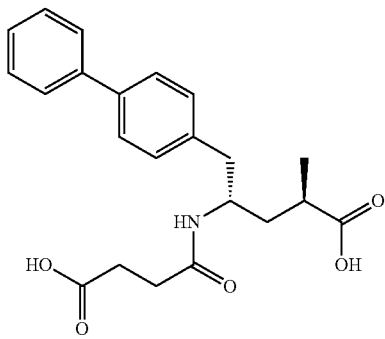

(III)

respectively, or in each case, a pharmaceutically acceptable salt thereof.

Preferred salts of the compound of formula (II) include, but are not limited to, a sodium salt disclosed in U.S. Pat. No. 5,217,996; and a triethanolamine or a tris(hydroxymethyl)aminomethane salt disclosed in WO 03/059345.

The subject matter relating to NEP inhibitors referred herein above, e.g., in U.S. patents and EP, GB, JP or WO patent applications, is herewith incorporated by reference, especially the subject matter corresponding to NEP inhibitors, and pharmaceutically acceptable salts and the preparation of the NEP inhibitors and pharmaceutical compositions thereof, that are disclosed herein.

Pro-drug derivatives of any compound of the invention are derivatives of said compounds which following administration release the parent compound in vivo via some chemical or physiological process, e.g., a pro-drug on being brought to the physiological pH or through enzyme action is converted to the parent compound. Exemplary pro-drug derivatives are, e.g., esters of free carboxylic acids and S-acyl and O-acyl derivatives of thiols, alcohols or phenols. Preferred are pharmaceutically acceptable ester derivatives convertible by solvolysis under physiological conditions to the parent carboxylic acid, e.g., lower alkyl esters, cycloalkyl esters, lower alkenyl esters, benzyl esters, mono- or di-substituted lower alkyl esters, such as the omega-(amino, mono- or di-lower alkylamino, carboxy, lower alkoxycarbonyl)-lower alkyl esters, the alpha-(lower alkanoyloxy, lower alkoxycarbonyl or di-lower alkylaminocarbonyl)-lower alkyl esters, such as the pivaloyloxymethyl ester and the like conventionally used in the art.

In view of the close relationship between the free compounds, the pro-drug derivatives and the compounds in the form of their salts, whenever a compound is referred to in this context, a pro-drug derivative and a corresponding salt is also intended, provided such is possible or appropriate under the circumstances.

In any of the aspects mentioned throughout this specification, the term "a NEP inhibitor" or "the NEP inhibitor" preferably refers to N-(3-carboxy-1-oxopropyl)-(4S)-p-phenylphenylmethyl)-4-amino-(2R)-methylbutanoic acid or a pharmaceutically acceptable salt thereof; and the term "a NEP inhibitor pro-drug" or "the NEP inhibitor pro-drug" preferably refers to N-(3-carboxy-1-oxopropyl)-(4S)-p-phenylphenylmethyl)-4-amino-(2R)-methylbutanoic acid ethyl ester or a pharmaceutically acceptable salt thereof.

With regard to the especially suitable NEP inhibitor pro-drug N-(3-carboxy-1-oxopropyl)-(4S)-p-phenylphenylmethyl)-4-amino-(2R)-methylbutanoic acid ethyl ester and the NEP inhibitor N-(3-carboxy-1-oxopropyl)-(4S)-p-phenylphenylmethyl)-4-amino-(2R)-methylbutanoic acid, and pharmaceutically acceptable salts thereof, in the context of the present invention, these can be used either alone or for patients which are already been treated with an Angiotensin Receptor Blocker.

The Angiotensin Receptor Blocker can be any known in the art, such as valsartan, irbesartan, losartan, olmesartan, eprosartan, telmisartan, azilsartan or a pharmaceutical acceptable salt thereof. Preferably, the NEP inhibitor pro-drug or NEP inhibitor is used in patients already treated with valsartan or a pharmaceutically acceptable salt thereof.

In one embodiment of the invention, and for all of its uses, the NEP inhibitor pro-drug or NEP inhibitor is administered together, concomitantly or sequentially with the Angiotensin Receptor Blocker valsartan or a pharmaceutically acceptable salt thereof. Preferably the NEP inhibitor pro-drug or the NEP inhibitor and the Angiotensin Receptor Blocker valsartan are administered in a 1:1 molar ratio.

In one embodiment of the invention, the NEP inhibitor pro-drug and the angiotensin receptor blocker are delivered together by administration of trisodium[3-((1S,3R)-1-biphenyl-4-ylmethyl-3-ethoxycarbonyl-1-butylcarbamoyl) propionate-(S)-3'-methyl-2'-(pentanoyl{2"-(tetrazol-5-ylate)biphenyl-4'-ylmethyl}amino)butyrate]hemipentahydrate (LCZ696). LCZ696 and formulations containing it are described and disclosed in international patent applications WO 2007/056546 and WO 2009/061713, which are herewith incorporated by reference.

Pharmaceutical Compositions

In another aspect the present invention also provides pharmaceutical compositions comprising a NEP inhibitor as defined herein above or a pharmaceutically acceptable salt or ester thereof, or pro-drug thereof, preferably the NEP inhibitor pro-drug N-(3-carboxy-1-oxopropyl)-(4S)-p-phenylphenylmethyl)-4-amino-(2R)-methylbutanoic acid ethyl ester or the NEP inhibitor N-(3-carboxy-1-oxopropyl)-(4S)-p-phenylphenylmethyl)-4-amino-(2R)-methylbutanoic acid, or pharmaceutically acceptable salts thereof, and one or more pharmaceutically acceptable carrier or excipient, for use in the treatment, prevention or delay of progression of a disease characterized and/or manifested by atrial enlargement and/or remodeling.

Furthermore, the present invention relates to pharmaceutical compositions comprising a NEP inhibitor, or a pharmaceutically acceptable salt or ester thereof, or pro-drug thereof, preferably the NEP inhibitor pro-drug N-(3-carboxy-1-oxopropyl)-(4S)-p-phenylphenylmethyl)-4-amino-(2R)-methylbutanoic acid ethyl ester or the NEP inhibitor N-(3-carboxy-1-oxopropyl)-(4S)-p-phenylphenylmethyl)-4-amino-(2R)-methylbutanoic acid, or pharmaceutically acceptable salts thereof, and one or more pharmaceutically acceptable carrier or excipient, for use in the reduction of the left atrial volume, the left atrial volume index (LAVI) and/or the left atrial dimension in patients suffering from a disease characterized and/or manifested by atrial enlargement and/or remodeling.

Diseases characterized by atrial enlargement and/or remodeling include, but are not limited to heart failure with preserved ejection fraction (HF-PEF), heart failure with reduced ejection fraction (HF-REF), cardiac dysrhythmias comprising atrial fibrillation, new onset atrial fibrillation and recurrent atrial fibrillation; mitral stenosis and regurgitation, cardiomyopathies, hypertension or pulmonary heart diseases.

In one embodiment, diseases characterized by atrial enlargement and/or remodeling include, but are not limited to, heart failure with preserved ejection fraction (HF-PEF), cardiac dysrhythmias such as atrial fibrillation, new onset atrial fibrillation and recurrent atrial fibrillation, mitral regurgitation, cardiomegalies, cardiomyopathies or pulmonary heart diseases.

In one embodiment of the invention the disease characterized by atrial enlargement and remodeling is heart failure with preserved ejection fraction (HF-PEF).

The invention also relates to pharmaceutical compositions comprising a NEP inhibitor, or a pharmaceutically acceptable salt or ester thereof, or pro-drug thereof, preferably the NEP inhibitor pro-drug N-(3-carboxy-1-oxopropyl)-(4S)-p-phenylphenylmethyl)-4-amino-(2R)-methylbutanoic acid ethyl ester or the NEP inhibitor N-(3-carboxy-1-oxopropyl)-(4S)-p-phenylphenylmethyl)-4-amino-(2R)-methylbutanoic acid, or pharmaceutically acceptable salts thereof, and one or more pharmaceutically acceptable carrier or excipient, for use in the improvement, stabilization or delayed worsening in NYHA classification of patients suffering from heart failure.

In one embodiment patients suffering from heart failure are patients suffering from heart failure with preserved ejection fraction (HF-PEF) or heart failure with reduced ejection fraction (HF-REF). In one embodiment patients suffering from heart failure are patients suffering from heart failure with preserved ejection fraction (HF-PEF).

In one embodiment, the invention also relates to a pharmaceutical composition comprising a NEP inhibitor, or a pharmaceutically acceptable salt or ester thereof, or pro-drug thereof, preferably the NEP inhibitor pro-drug N-(3-carboxy-1-oxopropyl)-(4S)-p-phenylphenylmethyl)-4-amino-(2R)-methylbutanoic acid ethyl ester or the NEP inhibitor N-(3-carboxy-1-oxopropyl)-(4S)-p-phenylphenylmethyl)-4-amino-(2R)-methylbutanoic acid, or pharmaceutically acceptable salts thereof, wherein the composition is for the treatment or prevention of atrial fibrillation or for the prevention of or for delaying the time until new onset of atrial fibrillation.

In a further embodiment, the pharmaceutical composition comprising a NEP inhibitor, or a pharmaceutically acceptable salt or ester thereof, or pro-drug thereof, preferably the NEP inhibitor pro-drug N-(3-carboxy-1-oxopropyl)-(4S)-p-phenylphenylmethyl)-4-amino-(2R)-methylbutanoic acid ethyl ester or the NEP inhibitor N-(3-carboxy-1-oxopropyl)-(4S)-p-phenylphenylmethyl)-4-amino-(2R)-methylbutanoic acid, or pharmaceutically acceptable salts thereof, wherein the composition is for the treatment or prevention of atrial fibrillation or for the prevention of or for delaying the time until new onset of atrial fibrillation in patients suffering from a disease characterized and/or manifested by atrial enlargement and/or remodeling.

In another embodiment, the pharmaceutical composition comprising the NEP inhibitor, or a pharmaceutically acceptable salt or ester thereof, or pro-drug thereof, preferably the NEP inhibitor pro-drug N-(3-carboxy-1-oxopropyl)-(4S)-p-phenylphenylmethyl)-4-amino-(2R)-methylbutanoic acid ethyl ester or the NEP inhibitor N-(3-carboxy-1-oxopropyl)-(4S)-p-phenylphenylmethyl)-4-amino-(2R)-methylbutanoic acid, or pharmaceutically acceptable salts thereof, is for the treatment or prevention of atrial fibrillation or for the prevention of or for delaying the time until new onset of atrial fibrillation in patients suffering from heart failure. In one embodiment patients suffering from heart failure are patients suffering from heart failure with preserved ejection fraction (HF-PEF) or heart failure with reduced ejection fraction (HF-REF). In one embodiment patients suffering from heart failure are patients suffering from heart failure with preserved ejection fraction (HF-PEF).

In one embodiment of the invention, the pharmaceutical composition comprising the NEP inhibitor, or a pharmaceutically acceptable salt or ester thereof, or pro-drug thereof, preferably the NEP inhibitor pro-drug N-(3-carboxy-1-oxopropyl)-(4S)-p-phenylphenylmethyl)-4-amino-(2R)-methylbutanoic acid ethyl ester or the NEP inhibitor N-(3-carboxy-1-oxopropyl)-(4S)-p-phenylphenylmethyl)-4-amino-(2R)-methylbutanoic acid, or pharmaceutically acceptable salts thereof, is for the treatment of patients suffering from heart failure with preserved ejection fraction (HF-PEF) with no history of atrial fibrillation.

In one embodiment of the invention, the pharmaceutical composition comprising the NEP inhibitor, or a pharmaceutically acceptable salt or ester thereof, or pro-drug thereof, preferably the NEP inhibitor pro-drug N-(3-carboxy-1-oxopropyl)-(4S)-p-phenylphenylmethyl)-4-amino-(2R)-methylbutanoic acid ethyl ester or the NEP inhibitor N-(3-carboxy-1-oxopropyl)-(4S)-p-phenylphenylmethyl)-4-amino-(2R)-methylbutanoic acid, or pharmaceutically acceptable salts thereof, is for the treatment of patients suffering from heart failure with preserved ejection fraction (HF-PEF) with no history of atrial fibrillation, wherein the NEP inhibitor pro-drug or NEP inhibitor prevents or delays the time to the new onset of atrial fibrillation.

In one embodiment thereof, the pharmaceutical composition comprising the NEP inhibitor, or a pharmaceutically acceptable salt or ester thereof, or pro-drug thereof, preferably the NEP inhibitor pro-drug N-(3-carboxy-1-oxopropyl)-(4S)-p-phenylphenylmethyl)-4-amino-(2R)-methylbutanoic acid ethyl ester or the NEP inhibitor N-(3-carboxy-1-oxopropyl)-(4S)-p-phenylphenylmethyl)-4-amino-(2R)-methylbutanoic acid, or pharmaceutically acceptable salts thereof, is superior to valsartan alone and/or enalapril alone in delaying the time to the new onset of atrial fibrillation.

In one embodiment of the invention, the pharmaceutical composition comprising the NEP inhibitor, or a pharmaceutically acceptable salt or ester thereof, or pro-drug thereof, preferably the NEP inhibitor pro-drug N-(3-carboxy-1-oxopropyl)-(4S)-p-phenylphenylmethyl)-4-amino-(2R)-methylbutanoic acid ethyl ester or the NEP inhibitor N-(3-carboxy-1-oxopropyl)-(4S)-p-phenylphenylmethyl)-4-amino-(2R)-methylbutanoic acid, or pharmaceutically acceptable salts thereof, is for reducing the level of plasma NT-proBNP in patients suffering from a disease characterized and/or manifested by atrial enlargement and/or remodeling, such as heart failure, in particular heart failure with preserved ejection fraction.

In another embodiment of the invention, the pharmaceutical composition comprising the NEP inhibitor, or a pharmaceutically acceptable salt or ester thereof, or pro-drug thereof, preferably the NEP inhibitor pro-drug N-(3-carboxy-1-oxopropyl)-(4S)-p-phenylphenylmethyl)-4-amino-(2R)-methylbutanoic acid ethyl ester or the NEP inhibitor N-(3-carboxy-1-oxopropyl)-(4S)-p-phenylphenylmethyl)-4-amino-(2R)-methylbutanoic acid, or pharmaceutically acceptable salts thereof,—when administered or used in the context of the invention—leads to a sustained reduction in plasma NT-proBNP concentration.

In the context of the present invention and all the aforementioned embodiments, the pharmaceutical composition comprising the NEP inhibitor, or a pharmaceutically acceptable salt or ester thereof, or pro-drug thereof, preferably the NEP inhibitor pro-drug N-(3-carboxy-1-oxopropyl)-(4S)-p-phenylphenylmethyl)-4-amino-(2R)-methylbutanoic acid ethyl ester or the NEP inhibitor N-(3-carboxy-1-oxopropyl)-(4S)-p-phenylphenylmethyl)-4-amino-(2R)-methylbutanoic acid, or pharmaceutically acceptable salts thereof, can in addition be used for the improvement, stabilization or delayed worsening in NYHA classification of patients suffering from heart failure.

In one embodiment said patients suffering from heart failure are patients suffering from heart failure with preserved ejection fraction (HF-PEF) or heart failure with reduced ejection fraction (HF-REF). In one embodiment said patients suffering from heart failure are patients suffering from heart failure with preserved ejection fraction (HF-PEF).

The pharmaceutical compositions for use according to the present invention comprise a therapeutically effective amount of a NEP inhibitor as defined herein above or a pharmaceutically acceptable salt or ester thereof, or pro-drug thereof. Each dosage unit can contain the daily dose or may contain a fraction of the daily dose, such as one-half or one-third of the dose.

In one embodiment, the pharmaceutical composition comprises the NEP inhibitor pro-drug N-(3-carboxy-1-oxopropyl)-(4S)-p-phenylphenylmethyl)-4-amino-(2R)-methylbutanoic acid ethyl ester or the NEP inhibitor N-(3-carboxy-1-oxopropyl)-(4S)-p-phenylphenylmethyl)-4-amino-(2R)-methylbutanoic acid, or pharmaceutically acceptable salts thereof.

In one embodiment, the pharmaceutical composition of the present invention can be used for patients which are already been treated with an Angiotensin Receptor Blocker as set out above.

In one embodiment of the invention for all of its uses, the pharmaceutical composition comprises the NEP inhibitor pro-drug N-(3-carboxy-1-oxopropyl)-(4S)-p-phenylphenylmethyl)-4-amino-(2R)-methylbutanoic acid ethyl ester or the NEP inhibitor N-(3-carboxy-1-oxopropyl)-(4S)-p-phenylphenylmethyl)-4-amino-(2R)-methylbutanoic acid, or pharmaceutically acceptable salts thereof, and the Angiotensin Receptor Blocker valsartan or a pharmaceutically acceptable salt thereof. Such combinations are for example disclosed within international patent application WO 2003/059345, which is herewith incorporated by reference.

In one embodiment, the pharmaceutical composition comprises the NEP inhibitor pro-drug N-(3-carboxy-1-oxopropyl)-(4S)-p-phenylphenylmethyl)-4-amino-(2R)-methylbutanoic acid ethyl ester or the NEP inhibitor N-(3-carboxy-1-oxopropyl)-(4S)-p-phenylphenylmethyl)-4-amino-(2R)-methylbutanoic acid, or pharmaceutically acceptable salts thereof, and the Angiotensin Receptor Blocker valsartan or a pharmaceutically acceptable salt thereof, in a 1:1 molar ratio.

In a further embodiment of the invention, the pharmaceutical compositions for use according to the present invention deliver the NEP inhibitor pro-drug and the angiotensin receptor blocker together to the patient upon administration by comprising trisodium[3-(((1S,3R)-1-biphenyl-4-ylmethyl-3-ethoxycarbonyl-1-butylcarbamoyl) propionate-(S)-3'-methyl-2'-(pentanoyl{2''-(tetrazol-5-ylate)biphenyl-4'-ylmethyl}amino)butyrate]hemipentahydrate (LCZ696). LCZ696 and formulations comprising it are described and disclosed in international patent applications WO 2007/056546 and WO 2009/061713.

The pharmaceutical compositions according to the invention can be prepared in a manner known per se and are those suitable for enteral, such as oral or rectal, and parenteral administration to mammals (warm-blooded animals), including man, comprising a therapeutically effective amount of the pharmacologically active compound, alone or in combination with one or more pharmaceutically acceptable carriers, especially suitable for enteral or parenteral application.

The pharmaceutical preparations of the invention contain, for example, from about 0.1% to about 100%, e. g. 80% or 90%, or from about 1% to about 60%, of the active ingredient. The term "about" or "approximately", as used herein in each instance, shall have the meaning of within 10%, more preferably within 5%, of a given value or range.

Pharmaceutical preparations according to the invention for enteral or parenteral administration are, e.g., those in unit dose forms, such as sugar-coated tablets, tablets, capsules, bars, sachets, granules, syrups, aqueous or oily suspensions or suppositories and furthermore ampoules. These are prepared in a manner known per se, e. g. by means of conventional mixing, granulating, sugar-coating, dissolving or lyophilizing processes. Thus, pharmaceutical preparations for oral use can be obtained by combining the active ingredient with solid carriers, if desired granulating a mixture obtained, and processing the mixture or granules, if desired or necessary, after addition of suitable excipients to give tablets or sugar-coated tablet cores.

Tablets may be formed from the active compound with fillers, for example calcium phosphate; disintegrating agents, for example maize starch, lubricating agents, for example magnesium stearate; binders, for example microcrystalline cellulose or polyvinylpyrrolidone and other optional ingredients known in the art to permit tabletting the mixture by known methods. Similarly, capsules, for example hard or soft gelatin capsules, containing the active compound with or without added excipients, may be prepared by known methods. The contents of the capsule may be formulated using known methods so as to give sustained release of the active compound.

Other dosage forms for oral administration include, for example, aqueous suspensions containing the active compound in an aqueous medium in the presence of a non-toxic suspending agent such as sodium carboxymethylcellulose, and oily suspensions containing the active compounds in a suitable vegetable oil, for example arachis oil.

The active compound may be formulated into granules with or without additional excipients. The granules may be ingested directly by the patient or they may be added to a suitable liquid carrier (e.g. water) before ingestion. The granules may contain disintegrants, e.g. an effervescent pair formed from an acid and a carbonate or bicarbonate salt to facilitate dispersion in the liquid medium.

The dosage of the active ingredient of the composition will, of course, vary with the nature of the severity of the condition to be treated and with the particular compound in the composition and its route of administration. It will also vary according to the age, weight and response of the individual patient.

Furthermore, the invention relates to a commercial package comprising a NEP inhibitor, or a pharmaceutically acceptable salt or ester thereof, or pro-drug thereof, preferably the NEP inhibitor pro-drug N-(3-carboxy-1-oxopropyl)-(4S)-p-phenylphenylmethyl)-4-amino-(2R)-methylbutanoic acid ethyl ester or the NEP inhibitor N-(3-carboxy-1-oxopropyl)-(4S)-p-phenylphenylmethyl)-4-amino-(2R)-methylbutanoic acid, or pharmaceutically acceptable salts thereof, and a package insert or other labeling including directions for treating a disease characterized and/or manifested by atrial enlargement and/or remodeling by administering a NEP inhibitor, or a pharmaceutically acceptable salt or ester thereof, or pro-drug thereof, to a patient in need thereof.

In a preferred embodiment, the package insert or other labeling including directions for treating a disease characterized and/or manifested by atrial enlargement and/or remodeling by administering a therapeutically effective amount of a NEP inhibitor, or a pharmaceutically acceptable salt or ester thereof, or pro-drug thereof, preferably the NEP inhibitor pro-drug N-(3-carboxy-1-oxopropyl)-(4S)-p-phenylphenylmethyl)-4-amino-(2R)-methylbutanoic acid ethyl ester or the NEP inhibitor N-(3-carboxy-1-oxopropyl)-(4S)-p-phenylphenylmethyl)-4-amino-(2R)-methylbutanoic acid, or pharmaceutically acceptable salts thereof, to a patient in need thereof.

In general, the daily dose range of the NEP inhibitor or a pharmaceutically acceptable salt or ester thereof, or pro-drug thereof, preferably the NEP inhibitor pro-drug N-(3-carboxy-1-oxopropyl)-(4S)-p-phenylphenylmethyl)-4-amino-(2R)-methylbutanoic acid ethyl ester or the NEP inhibitor N-(3-carboxy-1-oxopropyl)-(4S)-p-phenylphenylmethyl)-4-amino-(2R)-methylbutanoic acid, or pharmaceutically acceptable salts thereof, lies within the range of from about 0.01 mg/kg to about 100 mg/kg, preferably from about 0.1 mg/kg to about 50 mg/kg body weight of a subject in single or divided doses. In one embodiment, the daily dose range of the NEP inhibitor is from about 0.1 mg/kg to about 25 mg/kg, or from about 1 mg/kg to about 25 mg/kg body weight of a subject in single or divided doses. On the other hand, it may be necessary to use dosages outside these limits in some cases.

In the case where an oral composition is employed, a suitable dosage range of the NEP inhibitor or a pharmaceutically acceptable salt or ester thereof, or pro-drug thereof, preferably the NEP inhibitor pro-drug N-(3-carboxy-1-oxopropyl)-(4S)-p-phenylphenylmethyl)-4-amino-(2R)-methylbutanoic acid ethyl ester or the NEP inhibitor N-(3-carboxy-1-oxopropyl)-(4S)-p-phenylphenylmethyl)-4-amino-(2R)-methylbutanoic acid, or pharmaceutically acceptable salts thereof, is, e.g. from about 0.01 mg/kg to about 100 mg/kg in the composition per day, preferably from about 0.01 mg to about 2000 mg per day. For oral administration, the compositions are preferably provided in the form of tablets containing from about 0.01 mg to about 2,000 mg, e.g. about 0.01, about 0.05, about 0.1, about 0.2, about 0.5, about 1.0, about 2.5, about 5, about 10, about 15, about 20, about 25, about 30, about 40, about 50, about 75, about 100, about 125, about 150, about 175, about 200, about 225, about 250, about 500, about 750, about 850, about 1000 or about 2000 milligrams of the active ingredient. This dosage regimen may be adjusted to provide the optimal therapeutic response. For example, the NEP-inhibitor may be administered once daily over a period of several days, several (1, 2, 3, 4, or more) weeks or even longer. In another embodiment, the NEP-inhibitor is administered once, or several (e.g. 1, 2, 3) times daily.

Preferably, said tablets contain from about 10 mg to about 1000 mg, more preferably from about 10 mg to about 500 mg, most preferably from about 20 mg to about 250 mg, such as for example about 10 mg, about 15 mg, about 20 mg, about 25 mg, about 30 mg, about 40 mg, about 50 mg, about 75 mg, about 100 mg, about 125 mg, about 150 mg, about 175 mg, about 200 mg, about 225 mg, about 250 mg of the active ingredient, which is preferably the NEP inhibitor pro-drug N-(3-carboxy-1-oxopropyl)-(4S)-p-phenylphenylmethyl)-4-amino-(2R)-methylbutanoic acid ethyl ester or the NEP inhibitor N-(3-carboxy-1-oxopropyl)-(4S)-p-phenylphenylmethyl)-4-amino-(2R)-methylbutanoic acid, or pharmaceutically acceptable salts thereof.

In one embodiment the NEP inhibitor or a pharmaceutically acceptable salt or ester thereof, or pro-drug thereof, is administered twice daily.

In another embodiment the tablet contains 100 mg of the NEP inhibitor or a pharmaceutically acceptable salt or ester thereof, or pro-drug thereof, preferably the NEP inhibitor pro-drug N-(3-carboxy-1-oxopropyl)-(4S)-p-phenylphenylmethyl)-4-amino-(2R)-methylbutanoic acid ethyl ester or the NEP inhibitor N-(3-carboxy-1-oxopropyl)-(4S)-p-phenylphenylmethyl)-4-amino-(2R)-methylbutanoic acid, or pharmaceutically acceptable salts thereof, and is administered twice daily.

In one embodiment, when the NEP inhibitor or a pharmaceutically acceptable salt or ester thereof, or pro-drug thereof, preferably the NEP inhibitor pro-drug N-(3-carboxy-1-oxopropyl)-(4S)-p-phenylphenylmethyl)-4-amino-(2R)-methylbutanoic acid ethyl ester or the NEP inhibitor N-(3-carboxy-1-oxopropyl)-(4S)-p-phenylphenylmethyl)-4-amino-(2R)-methylbutanoic acid, or pharmaceutically acceptable salts thereof, is co-administered with the angiotensin receptor blocker valsartan or a pharmaceutically acceptable salt thereof, the dose of the angiotension receptor blocker valsartan is as follows: Valsartan is preferably used in the form of an oral composition, preferably provided in the form of tablets (e.g. in the form of the approved drug known under the trademark DIOVAN®), containing from about 0.01 mg to about 2000 mg, e.g. about 0.01, about 0.05, about 0.1, about 0.2, about 0.5, about 1.0, about 2.5, about 5, about 10, about 15, about 20, about 25, about 30, about 40, about 50, about 75, about 100, about 125, about 150, about 175, about 200, about 225, about 250, about 500, about 750, about 850, about 1000 or about 2000 milligrams of the active ingredient.

Preferably, said valsartan tablets contain from about 10 mg to about 1000 mg, more preferably from about 10 mg to about 500 mg, most preferably from about 20 mg to about 250 mg, such as for example about 10 mg, about 15 mg, about 20 mg, about 25 mg, about 30 mg, about 40 mg, about 50 mg, about 75 mg, about 100 mg, about 125 mg, about 150 mg, about 175 mg, about 200 mg, about 225 mg, about 250 mg of the active ingredient. In a particular embodiment, such valsartan tablets comprise 80 mg, 160 mg, 320 mg or 640 mg of active ingredient.

In the embodiments where the NEP inhibitor pro-drug is provided in the form of LCZ696 as trisodium[3-((1S,3R)-1-biphenyl-4-ylmethyl-3-ethoxycarbonyl-1-butylcarbamoyl) propionate-(S)-3'-methyl-2'-(pentanoyl{2"-(tetrazol-5-ylate)biphenyl-4'-ylmethyl}amino)butyrate] hemipentahydrate in the pharmaceutical compositions for use in the context of the present invention, the unit dose of the therapeutic agents N-(3-carboxy-1-oxopropyl)-(4S)-p-phenylphenylmethyl)-4-amino-(2R)-methylbutanoic acid ethyl ester and valsartan together will be in the range from about 1 to about 1000 mg, such as 40 mg to 400 mg (e.g., 50 mg, 100 mg, 200 mg, 400 mg) per day. Alternatively lower doses may be given, for example doses of 0.5 to 100 mg; 0.5 to 50 mg; or 0.5 to 20 mg per day. (As explanatory note, a unit dose of 100 mg LCZ696 delivering 100 mg of the two agents N-(3-carboxy-1-oxopropyl)-(4S)-p-phenylphenylmethyl)-4-amino-(2R)-methylbutanoic acid ethyl ester and valsartan corresponds to 107.8 mg of trisodium [3-((1S,3R)-1-biphenyl-4-ylmethyl-3-ethoxycarbonyl-1-butylcarbamoyl) propionate-(S)-3'-methyl-2'-(pentanoyl{2"-(tetrazol-5-ylate)biphenyl-4'-ylmethyl}amino)butyrate] hemipentahydrate. Correspondingly, a unit dose of 200 mg requires 215.6 mg, and a unit dose of 400 mg requires 431.2 mg of trisodium[3-((1S,3R)-1-biphenyl-4-ylmethyl-3- ethoxycarbonyl-1-butylcarbamoyl) propionate-(S)-3'-methyl-2'-(pentanoyl{2"-(tetrazol-5-ylate)biphenyl-4'-ylmethyl}amino)butyrate]hemipentahydrate.

Method of Treatment

The present invention also relates to a method for treatment, the prevention or delay of progression of a disease characterized and/or manifested by atrial enlargement and/or remodeling comprising administration of a therapeutically effective amount, or a prophylactically effective amount, of a NEP inhibitor, or a pharmaceutically acceptable salt or ester thereof, or pro-drug thereof, preferably the NEP inhibitor pro-drug N-(3-carboxy-1-oxopropyl)-(4S)-p-phenylphenylmethyl)-4-amino-(2R)-methylbutanoic acid ethyl ester or the NEP inhibitor N-(3-carboxy-1-oxopropyl)-(4S)-p-phenylphenylmethyl)-4-amino-(2R)-methylbutanoic acid, or pharmaceutically acceptable salts thereof, to a subject, e.g. a human subject, in need of such treatment.

The present invention also relates to a method for the reduction of the left atrial volume, the left atrial volume index (LAVI) and/or the left atrial dimension in patients suffering from a disease characterized and/or manifested by atrial enlargement and/or remodeling comprising administration of a therapeutically effective amount of a NEP inhibitor, or a pharmaceutically acceptable salt or ester thereof, or pro-drug thereof, preferably the NEP inhibitor pro-drug N-(3-carboxy-1-oxopropyl)-(4S)-p-phenylphenylmethyl)-4-amino-(2R)-methylbutanoic acid ethyl ester or the NEP inhibitor N-(3-carboxy-1-oxopropyl)-(4S)-p-phenylphenylmethyl)-4-amino-(2R)-methylbutanoic acid, or pharmaceutically acceptable salts thereof, to a subject, e.g. a human, in need of such treatment.

Diseases characterized by atrial enlargement and/or remodeling include, but are not limited to heart failure with preserved ejection fraction (HF-PEF), heart failure with reduced ejection fraction (HF-REF), cardiac dysrhythmias comprising atrial fibrillation, new onset atrial fibrillation and recurrent atrial fibrillation; mitral stenosis and regurgitation, cardiomyopathies, hypertension or pulmonary heart diseases.

In one embodiment, diseases characterized by atrial enlargement and/or remodeling include, but are not limited to, heart failure with preserved ejection fraction (HF-PEF), cardiac dysrhythmias such as atrial fibrillation, new onset atrial fibrillation and recurrent atrial fibrillation, mitral regurgitation, cardiomegalies, cardiomyopathies or pulmonary heart diseases.

In one embodiment said disease characterized and/or manifested by atrial enlargement and/or remodeling is heart failure with preserved ejection fraction (HF-PEF).

Furthermore, the present invention relates to a method for the improvement, stabilization or delayed worsening in NYHA classification of patients suffering from heart failure, comprising administration of a therapeutically effective amount of a NEP inhibitor, or a pharmaceutically acceptable salt or ester thereof, or pro-drug thereof, preferably the NEP inhibitor pro-drug N-(3-carboxy-1-oxopropyl)-(4S)-p-phenylphenylmethyl)-4-amino-(2R)-methylbutanoic acid ethyl ester or the NEP inhibitor N-(3-carboxy-1-oxopropyl)-(4S)-p-phenylphenylmethyl)-4-amino-(2R)-methylbutanoic acid, or pharmaceutically acceptable salts thereof, to a subject, e.g. a human, in need of such treatment.

In one embodiment patients suffering from heart failure are patients suffering from heart failure with preserved ejection fraction (HF-PEF) or heart failure with reduced ejection fraction (HF-REF). In one embodiment patients suffering from heart failure are patients suffering from heart failure with preserved ejection fraction (HF-PEF).

The present invention also relates to a method for the treatment or prevention of atrial fibrillation or for the prevention of or for delaying the time until new onset of atrial fibrillation comprising administration of a therapeutically effective amount, or a prophylactically effective amount, of a NEP inhibitor, or a pharmaceutically acceptable salt or ester thereof, or pro-drug thereof, preferably the NEP inhibitor pro-drug N-(3-carboxy-1-oxopropyl)-(4S)-p-phenylphenylmethyl)-4-amino-(2R)-methylbutanoic acid ethyl ester or the NEP inhibitor N-(3-carboxy-1-oxopropyl)-(4S)-p-phenylphenylmethyl)-4-amino-(2R)-methylbutanoic acid, or pharmaceutically acceptable salts thereof, to a subject, e.g. a human subject, in need of such treatment.

In a further embodiment, the present invention relates to a method for the treatment or prevention of atrial fibrillation or for the prevention of or for delaying the time until new onset of atrial fibrillation comprising administration of a therapeutically effective amount, or a prophylactically effective amount, of a NEP inhibitor, or a pharmaceutically acceptable salt or ester thereof, or pro-drug thereof, preferably the NEP inhibitor pro-drug N-(3-carboxy-1-oxopropyl)-(4S)-p-phenylphenylmethyl)-4-amino-(2R)-methylbutanoic acid ethyl ester or the NEP inhibitor N-(3-carboxy-1-oxopropyl)-(4S)-p-phenylphenylmethyl)-4-amino-(2R)-methylbutanoic acid, or pharmaceutically acceptable salts thereof, to a patient suffering from a disease characterized and/or manifested by atrial enlargement and/or remodeling.

In another embodiment, the present invention relates to a method for the treatment or prevention of atrial fibrillation or for the prevention of or for delaying the time until new onset of atrial fibrillation comprising administration of a therapeutically effective amount, or a prophylactically effective amount, of a NEP inhibitor, or a pharmaceutically acceptable salt or ester thereof, or pro-drug thereof, preferably the NEP inhibitor pro-drug N-(3-carboxy-1-oxopropyl)-(4S)-p-phenylphenylmethyl)-4-amino-(2R)-methylbutanoic acid ethyl ester or the NEP inhibitor N-(3-carboxy-1-oxopropyl)-(4S)-p-phenylphenylmethyl)-4-amino-(2R)-methylbutanoic acid, or pharmaceutically acceptable salts thereof, to a patient suffering from heart failure. In one embodiment patients suffering from heart failure are patients suffering from heart failure with preserved ejection fraction (HF-PEF) or heart failure with reduced ejection fraction (HF-REF). In one embodiment patients suffering from heart failure are patients suffering from heart failure with preserved ejection fraction (HF-PEF).

In one embodiment of the invention the method comprises administration of a therapeutically effective amount, or a prophylactically effective amount, of a NEP inhibitor, or a pharmaceutically acceptable salt or ester thereof, or pro-drug thereof, preferably the NEP inhibitor pro-drug N-(3-carboxy-1-oxopropyl)-(4S)-p-phenylphenylmethyl)-4-amino-(2R)-methylbutanoic acid ethyl ester or the NEP inhibitor N-(3-carboxy-1-oxopropyl)-(4S)-p-phenylphenylmethyl)-4-amino-(2R)-methylbutanoic acid, or pharmaceutically acceptable salts thereof, to a patient suffering from heart failure with preserved ejection fraction (HF-PEF) with no history of atrial fibrillation.

In one embodiment, the invention relates to a method for treatment comprising administration of a therapeutically effective amount, or a prophylactically effective amount, of a NEP inhibitor, or a pharmaceutically acceptable salt or ester thereof, or pro-drug thereof, preferably the NEP inhibitor pro-drug N-(3-carboxy-1-oxopropyl)-(4S)-p-phenylphenylmethyl)-4-amino-(2R)-methylbutanoic acid ethyl ester or the NEP inhibitor N-(3-carboxy-1-oxopropyl)-(4S)-p-phenylphenylmethyl)-4-amino-(2R)-methylbutanoic acid, or pharmaceutically acceptable salts thereof, to patients suffering from heart failure with preserved ejection fraction (HF-PEF) with no history of atrial fibrillation, wherein the NEP inhibitor pro-drug or NEP inhibitor prevents or delays the time to the new onset of atrial fibrillation.

In one embodiment thereof, the administration of the NEP inhibitor pro-drug or NEP inhibitor is superior to valsartan alone and/or enalapril alone in delaying the time to the new onset of atrial fibrillation.

In one embodiment, the present invention relates to a method for reducing the level of plasma NT-proBNP in patients comprising administration of a therapeutically effective amount, or a prophylactically effective amount, of a NEP inhibitor, or a pharmaceutically acceptable salt or ester thereof, or pro-drug thereof, preferably the NEP inhibitor pro-drug N-(3-carboxy-1-oxopropyl)-(4S)-p-phenylphenylmethyl)-4-amino-(2R)-methylbutanoic acid ethyl ester or the NEP inhibitor N-(3-carboxy-1-oxopropyl)-(4S)-p-phenylphenylmethyl)-4-amino-(2R)-methylbutanoic acid, or pharmaceutically acceptable salts thereof, to said patient suffering from a disease characterized and/or manifested by atrial enlargement and/or remodeling, such as heart failure, in particular heart failure with preserved ejection fraction.

In another embodiment of the invention, the NEP inhibitor pro-drug or NEP inhibitor—when administered or used in the context of the invention—leads to a sustained reduction in plasma NT-proBNP concentration.

In the context of the present invention and all the aforementioned embodiments, the method comprising administration of a therapeutically effective amount, or a prophylactically effective amount, of a NEP inhibitor, or a pharmaceutically acceptable salt or ester thereof, or pro-drug thereof, preferably the NEP inhibitor pro-drug N-(3-carboxy-1-oxopropyl)-(4S)-p-phenylphenylmethyl)-4-amino-(2R)-methylbutanoic acid ethyl ester or the NEP inhibitor N-(3-carboxy-1-oxopropyl)-(4S)-p-phenylphenylmethyl)-4-amino-(2R)-methylbutanoic acid, or pharmaceutically acceptable salts thereof, to a patient in need thereof, is in addition used for the improvement, stabilization or delayed worsening in NYHA classification of patients suffering from heart failure.

In one embodiment said patients suffering from heart failure are patients suffering from heart failure with preserved ejection fraction (HF-PEF) or heart failure with reduced ejection fraction (HF-REF). In one embodiment said patients suffering from heart failure are patients suffering from heart failure with preserved ejection fraction (HF-PEF).

The following example is illustrative, but does not serve to limit the scope of the invention described herein.

Example 1

A 36-week, randomized, double-blind, multi-center, parallel group, active controlled study to evaluate the efficacy, safety, and tolerability of LCZ696 compared to valsartan in patients with chronic heart failure with preserved left-ventricular ejection fraction (HF-PEF).

LCZ696:

LCZ696 refers to the supramolecular complex trisodium [3-((1S,3R)-1-biphenyl-4-ylmethyl-3-ethoxycarbonyl-1-butylcarbamoyl) propionate-(S)-3'-methyl-2'-(pentanoyl{2''-(tetrazol-5-ylate)biphenyl-4'-ylmethyl}amino)butyrate] hemipentahydrate. This compound and pharmaceutical compositions thereof have been previously disclosed in WO2007/056546 and WO 2009/061713, whose preparative teachings are incorporated herein by reference.

LCZ696 is a first-in-class angiotensin receptor neprilysin inhibitor that comprises the molecular moieties of the NEP (neutral endopeptidase EC 3.4.24.11) inhibitor pro-drug AHU377 (N-(3-carboxy-1-oxopropyl)-(4S)-p-phenylphenylmethyl)-4-amino-(2R)-methylbutanoic acid ethyl ester) and the angiotensin receptor blocker valsartan as a single compound. AHU377 is metabolized by enzymatic cleavage to LBQ657 (N-(3-carboxy-1-oxopropyl)-(4S)-p-phenylphenylmethyl)-4-amino-(2R)-methylbutanoic acid), the active inhibitor of neutral endopeptidase, which is the major enzyme responsible for the breakdown of atrial natriuretic peptides.

Valsartan:

Valsartan or (S)-N-valeryl-N-{[2'-(1H-tetrazole-5-yl)-biphenyl-4-yl]-methyl}-valine) can be purchased from commercial sources or can be prepared according to known methods, such as described in U.S. Pat. No. 5,399,578 and EP 0443983, whose preparative teachings are incorporated by reference herein.

Study Design:

Men and women aged 40 years or older with a left ventricular ejection fraction of 45% or above, and a documented history of heart failure with associated signs or symptoms (dyspnea on exertion, orthopnea, paroxysmal dyspnea, and peripheral edema) are eligible. Patients are required to have an NT-proBNP >400 pg/mL at screening, be on diuretic therapy, and have a systolic blood pressure less than 140 mm Hg, or 160 mm Hg or less if on three or more blood pressure medications at randomization. Additional inclusion criteria include an estimated glomerular filtration rate (eGFR) of at least 30 ml/min/1.73 $m^2$ at screening (calculated by the Modification of Diet in Renal Disease formula) and a potassium of no more than 5.2 mmol/L.

Patients are excluded if they had prior left ventricular ejection fraction less than 45% at any time, isolated right heart failure due to pulmonary disease, dyspnea due to non-cardiac causes such as pulmonary disease, anemia, or severe obesity, primary valvular or myocardial diseases, or coronary artery or cerebrovascular disease requiring revascularization within 3 months of screening or likely to require revascularization during the trial.

Eligible patients are enrolled into a 2-week, single-blind placebo run-in period, during which time they continue their background medications. ACE inhibitors and angiotensin receptor blockers are required to be discontinued 24 hours prior to randomization. After two weeks, all patients who fulfill the inclusion/exclusion criteria are randomized to either LCZ696 or valsartan in a 1:1 ratio.

Patients are started on LCZ696 50 mg twice daily or valsartan 40 mg twice daily and are titrated to their final medication doses of LCZ696 200 mg twice daily or valsartan 160 mg twice daily over a period of 2 to 4 weeks. Patients are on their starting dose for 1 week and titrated up to either LCZ696 100 mg twice daily or valsartan 80 mg twice daily for 1 week. The maximum LCZ696 dose achieves exposures similar to a dose of valsartan that provides comparable AT1 blockade. At the investigator's discretion, patients are allowed to stay on each titration dose for an additional week. All patients are then titrated to their final doses of LCZ696 200 mg twice daily or valsartan 160 mg twice daily, in addition to standard background therapy. Patients remain on these doses for the remainder of the study, although those not tolerating the maximum dose of study medication could be down-titrated to a lower dose at the Investigator's discretion and then re-challenged to the maximum dose of study medication, or remain on the lower dose.

The dose selection reflects equal exposure of valsartan in both study arms as published by Gu et al., 2010, J Clin Pharmacol., 401-14 and Ruilope et al., 2010, Lancet, 375 (9722):1255-66.

Study Procedures:

The primary study endpoint is the change from baseline in NT-proBNP assessed at 12 weeks, and is analyzed using the last observation after baseline carried forward. Secondary endpoints include changes in echocardiographic measures (left ventricular volumes and ejection fraction, left atrial volume, measures of diastolic function), change in blood pressure, as well as change in New York Heart Association Class (NYHA) clinical composite assessment and quality of life (Kansas City Cardiomyopathy Questionnaire).

Echocardiographic studies are performed at screening, randomization, at week 12, and week 36 or at end of study or early termination visits. Echocardiograms performed at screening are evaluated by local readers for qualifying information. All other echocardiograms are only performed in patients meeting NT-proBNP entry criterion and are evaluated centrally. For assessment of global ventricular size and function, left ventricular end-diastolic and end-systolic volumes are obtained utilizing the Simpson's rule method and left ventricular ejection fraction is derived in the usual fashion. Maximal left atrial dimension is measured in the parasternal long-axis view, and left atrial volume is assessed with the Simpson's rule method and indexed to body surface area.

Measurements are made in triplicate in accordance with the recommendations of the American Society of Echocardiography. Blood pressure and heart rate are measured at all study visits with a calibrated standard sphygmomanometer and appropriate size cuff. The use of concomitant medication is recorded at each study visit.

The clinical composite assessment is based on a composite of the NYHA functional classification, patient global assessment and major adverse clinical events. Patients are classified as improved if at the endpoint visit they experienced improvement in NYHA functional classification or in patient global assessment (or both) but do not have a major adverse cardiovascular event. Patients are determined to be worse if at the endpoint visit they experienced a major adverse cardiac event during the double blind treatment or reported worsening of their NYHA class or patient global assessment. Patients are considered unchanged if they are neither improved nor worsened.

Results:

LCZ696 was well tolerated with adverse effects similar to valsartan.

Of 301 patients, 261 patients completed evaluation at 12 weeks and 241 patients at 36 weeks. The mean age was 71 years, 57% of patients were female, and the majority of patients were NYHA class II. Atrial fibrillation was present at baseline in 85 (28%) patients. Mean left ventricular ejection fraction (LVEF) was 58±7.7%, and LVEF was greater than 50% in 238 (87%) of patients. Blood pressure was well-controlled (mean sitting blood pressure 135/77 mm Hg, median sitting blood pressure 136/79 mm Hg). Baseline NT-proBNP was elevated (geometric mean 830.6 µg/mL, 95% CI 744-928). All patients were on diuretics at baseline and the majority of patients had been taking an ACE inhibitor or angiotensin receptor blocker prior to enrollment. Echocardiographic assessment at baseline demonstrated reduced mitral annular relaxation velocity, elevated E/e', and enlarged left atria, consistent with mild elevation of cardiac filling pressures.

The primary endpoint, change in NT-proBNP from baseline to 12 weeks, was significantly different in the LCZ696 group compared with the valsartan group (ratio of change LCZ696/valsartan 0.77, 95% CI 0.64-0.92, p=0.005; see Table 1) with a greater reduction in the LCZ696-treated patients.

Analysis of the primary endpoint in completers only (p=0.007) or with multiple imputation for missing values (p=0.01) yielded similar results. The effect of LCZ696 on NT-proBNP occurred fairly early, although an early reduction in NT-proBNP after 4 weeks of treatment in the LCZ696 group compared with the valsartan group was not significant (p=0.063). The reduction in NT-proBNP at 12 weeks was noted in all prespecified subgroups. Of these subgroups, only patients with diabetes had a differentially greater reduction in NT-proBNP when treated with LCZ696 compared with patients without diabetes (interaction p=0.02).

TABLE 1

NT-proBNP at baseline, 12 weeks, and 36 weeks, and ratio of change in NT-proBNP at 12 and 36 weeks

| | NT-proBNP (pg/ml) at 12 weeks | | | NT-proBNP (pg/ml) at 36 weeks | | |
| --- | --- | --- | --- | --- | --- | --- |
| | n | Baseline | 12 weeks | n | Baseline | 36 weeks |
| LCZ696 | 134 | 783 (670-914) | 605 (512-714) | 115 | 763 (646-901) | 496 (401-613) |
| Valsartan | 132 | 862 (733-1012) | 835 (710-981) | 116 | 822 (688-983) | 607 (484-760) |
| Ratio of change (LZC696/valsartan) | | | 0.77 (95% CI 0.64-0.92), p = 0.005 | | | 0.85 (95% CI 0.65-1.09), p = 0.20 |

Data for NT-proBNP are geometric mean (95% CI)

After 12 weeks of treatment, blood pressure was reduced by 9.3 (SD 14)/4.9 (10) mm Hg in the LCZ696 group and 2.9 (17)/2.1 (11) mm Hg in the valsartan group (p=0.001 for systolic and p=0.09 for diastolic blood pressure differences). LCZ696 was associated with a greater reduction in NT-proBNP than was valsartan even after adjustment for the change in blood pressure between the two groups (p=0.01). Moreover, change in blood pressure correlated poorly with change in NT-proBNP (r=0.104, p=0.1).

Minimal changes in echocardiographic parameters such as left ventricular size or function, diastolic function, left ventricular (LV) mass or tricuspid regurgitant velocity from baseline to 12 weeks between treatment groups has been observed. Left atrial dimension was numerically, but not significantly, reduced at 12 weeks.

Although NT-proBNP remained reduced from baseline at 36 weeks in the LCZ696 group (see Table 1), the difference between treatment groups at 36 weeks was no longer significant (p=0.20; Table 1). At 36 weeks, blood pressure was reduced by 7.5 (15)/5.1 (10.8) in the LCZ696 group versus 1.5 (16)/0.34 (11.5) in the valsartan group (p=0.006 for systolic and p=0.001 for diastolic blood pressure differences).

Left atrial volume and left atrial volume index (LAVI) was reduced significantly in the LCZ696 group after 36 weeks of treatment (p=0.003 and 0.007, for left atrial volume and LAVI respectively), as was left atrial dimension (p=0.034) (Table 2).

The change in left atrial size was most apparent in patients without atrial fibrillation at baseline. No other echocardiographic measures, including LVEF, ventricular volumes, left ventricular mass index, relative wall thickness, or measures of diastolic function, differed between treatment groups at 36 weeks.

TABLE 2

Changes in Echocardiographic Parameters at 36 weeks (Left atrial dimension (LA dimension), left atrial volume (LA Volume), left atrial volume index (LA Volume Index), left ventricle mass index (LA mass index) and relative wall thickness)

| | LCZ696 | | Valsartan | | |
|---|---|---|---|---|---|
| | Base-line | Δ from | Base-line | Δ from | p- |
| | N | Baseline | N | Baseline | value |
| LA dimension (cm) | 99 3.68 | −0.15 | 108 3.73 | −0.08 | 0.03 |
| LA Volume (ml) | 96 65.26 | −4.61 | 112 68.28 | 0.37 | 0.003 |
| LA Volume Index (ml/m$^2$) | 90 35.01 | −2.61 | 106 36.80 | 0.31 | 0.007 |
| LV mass index (g/m$^2$) | 91 76.56 | −2.78 | 100 79.45 | −1.93 | 0.35 |
| Relative wall thickness (%) | 98 0.37 | +0.01 | 107 0.37 | +0.01 | 0.96 |

NYHA class improvement at 12 weeks did not differ significantly between groups (p=0.11), but we noted an improvement in NYHA class at 36 weeks in the LCZ696 group compared with the valsartan group (p=0.05, FIG. 1).

Clinical composite assessment after 12 weeks (p=0.19) and 36 weeks (p=0.17) of treatment did not differ significantly between groups (FIG. 1). There was no difference in KCCQ score between treatment groups at either time point.

Target dose was achieved in 121 (81%) patients in the LCZ696 group and in 119 (78%) in the valsartan group. The use of concomitant blood-pressure lowering drugs, particularly loop diuretics, was greater in the valsartan group during the trial, although β-blocker use was similar. In the LCZ696 group, 22 patients (15%) had one or more serious adverse events, including one death; in the valsartan group, 30 patients (20%) had one or more serious adverse events, including two deaths. In the valsartan group, the adverse event "atrial fibrillation" was observed in 8 patients (5.3%), whereas in the LCZ696 group, only 2 patients (2.0%) experienced this adverse event.

The number of patients with hypotension, renal dysfunction, or hyperkalaemia did not differ between groups. Angiooedema occurred in one patient on LCZ696, who did not need admission to hospital, and no patients on valsartan.

Conclusion

In summary, in patients with heart failure with preserved ejection fraction, the angiotensin receptor neprilysin inhibitor LCZ696 reduced NT-proBNP to a greater extent than valsartan after 12 weeks of therapy. The reduction in NT-proBNP in patients receiving LCZ696 became evident at 4 weeks and was sustained to 36 weeks, though the between group difference was no longer statistically significant. We further observed a reduction in left atrial size, indicative of reverse left atrial remodeling, in patients randomized to LCZ696 after 36 weeks, compared with those randomized to valsartan. We observed trends in improvement in NYHA class in those patients randomized to LCZ696, which was overall well-tolerated. These findings indicate that a NEP inhibitor may have favorable effects in patients with HF-pEF.

In addition, the induction of reverse remodeling of the left atrium, i.e. the significant reductions in left atrial volume and left atrial dimension, upon treatment with LCZ696 provide a potential signal for the use of LCZ696 for treatment or prevention of atrial fibrillation and/or the reduction of new onset atrial fibrillation upon treatment with LCZ696 in comparison to other drugs currently being the standard of care. This hypothesis is further supported by the fact that the incidence of the adverse event atrial fibrillation was lower in the LCZ696 treated patient group than in the valsartan treated patient group.

Example 2

A randomized, double-blind, parallel group, active-controlled, two-arm, event-driven trial comparing the long-term efficacy and safety of enalapril and LCZ696 on morbidity and mortality in patients with chronic symptomatic heart failure and reduced ejection fraction (HF-REF) [PARADIGM-HF].

LCZ696: see Example 1

Enalapril

The ACE inhibitor Enalapril or (2S)-1-[(2S)-2-{[(2S)-1-ethoxy-1-oxo-4-phenylbutan-2-yl]amino}propanoyl]-pyrrolidine-2-carboxylic acid can be purchased from commercial sources or can be prepared according to known methods.

Objective & Methods:

Patients with chronic HF, NYHA functional class II-IV symptoms, an elevated plasma B-type natriuretic peptide (BNP) or NT-proBNP level and, initially, a left ventricular ejection fraction of ≤40% (later amended to ≤35%) are eligible. Patients enter a single blind enalapril run-in period (titrated to 10 mg bid) which, depending on tolerability, is followed by an LCZ696 run-in period (100 mg titrated to 200 mg bid). Then, patients tolerating both drugs at the target dose, are randomized 1:1 to either enalapril 10 mg bid or LCZ696 200 mg bid. The primary outcome is the composite of cardiovascular death or HF hospitalization, although the trial is powered to detect a 15% relative risk reduction in cardiovascular death with LCZ696, compared with enalapril. Secondary outcome measures are change in the Kansas City Cardiomyopathy Questionnaire (KCCQ) clinical summary score at 8 months, change in renal function, and time to all-cause mortality.

Study Design and Procedures

Detailed study design and procedures can be found under www.clinicaltrials.gov, study number NCT01035255, and as published in The European Journal of Heart Failure by McMurray et al (18 Apr. 2013) titled "Dual angiotensin receptor and neprilysin inhibition as an alternative to angiotensin converting enzyme inhibition in patients with chronic systolic heart failure: rationale for and design of the Prospective comparison of ARNI with ACEI to Determine Impact on Global Mortality and morbidity in Heart Failure trial (PARADIGM-HF)".

Example 3

A multicenter, randomized, double-blind, parallel group, active-controlled study to evaluate the efficacy and safety of LCZ696 compared to valsartan, on morbidity and mortality in heart failure patients (NYHA Class II-IV) with preserved ejection fraction [PARAGON-HF]
LCZ696: see Example 1
Valsartan: see Example 1
Background Heart failure with preserved ejection fraction (HFpEF) accounts for up to half of heart failure (HF) cases and is associated with substantial morbidity and mortality. To date both angiotensin converting enzyme inhibitors (ACEIs) and angiotensin receptor blockers (ARBs) have been tested in clinical trials in HFpEF and not been shown to improve the primary outcome. Several pathophysiologic mechanisms have been implicated in this disorder, including abnormalities of diastolic function and impaired natriuretic response to acute volume expansion.

LCZ696 is a first in class, angiotensin receptor neprilysin inhibitor (ARNI), providing systemic exposure to AHU377, a neprilysin (NEP) inhibitor and valsartan, an ARB. The potential clinical benefits from NEP inhibition can only be leveraged if the RAAS system is inhibited concomitantly.1, 2

The mechanisms of action of LCZ696 suggest that it may have an impact on the pathophysiology of HFpEF, in which it is believed that excessive fibrosis and myocyte hypertrophy lead to abnormal left ventricular relaxation and filling, impaired diastolic distensibility and/or increased vascular stiffness, with consequent elevated cardiac filling pressures.

The PARAMOUNT trial tested the safety and efficacy of LCZ696 in patients with HFpEF and showed a significant reduction in N-terminal pro-B-type natriuretic peptide (NT-proBNP) at 12 weeks and significant improvement in left atrial size and New York Heart Association (NYHA) class in patients randomized to LCZ696 compared to valsartan at 36 weeks. NT-proBNP is not a substrate for neprilysin.
Methods
 PARAGON-HF will assess the effect of LCZ696 on outcomes (cardiovascular [CV] death and total—first and recurrent—HF hospitalizations) in patients with HFpEF.
 Screening: up to 2 weeks
 Active Run-In Period: 3-8 weeks (can be shorter for patients previously exposed to standard doses of RAAS blockade; longer for patients with no prior exposure or on low doses of ACEIs or ARBs.)
 Double Blind Period: Projected 2.75 years enrollment; with a minimum of 2 years follow up
Primary and Secondary Objectives Primary objective: The primary objective of this trial is to compare LCZ696 to valsartan in reducing the rate of the composite endpoint of CV death and total (first and recurrent) HF hospitalizations, in HF patients (NYHA Class II-IV) with preserved EF (left ventricular ejection fraction [LVEF] ≥45%).
 Secondary objectives:
 To compare LCZ696 to valsartan in reducing the rate of the composite endpoint of CV death, total HF hospitalizations, total non-fatal strokes, and total non-fatal myocardial infarctions (MIs). Total is defined as the first and all recurrent events.
 To compare LCZ696 to valsartan in improving NYHA functional classification at 8 months.
 To compare LCZ696 to valsartan in delaying the time to new onset AF in patients with no history of AF and without AF on electrocardiogram (ECG) at baseline.
 To compare LCZ696 to valsartan in delaying the time to all-cause mortality.
Study Design and Detailed Procedures Detailed study design and procedures can be found under www.clinicaltrials.gov, study number NCT01920711.

The invention claimed is:

1. A method for the treatment or delay of progression of a disease characterized by atrial enlargement and/or remodeling in a human patient comprising administration of a therapeutically effective amount of the NEP inhibitor pro-drug N-(3-carboxy-1-oxopropyl)-(4S)-p-phenylphenylmethyl)-4-amino-(2R)-methylbutanoic acid ethyl ester, or a pharmaceutically acceptable salt thereof; or the NEP inhibitor N-(3-carboxy-1-oxopropyl)-(4S)-p-phenylphenylmethyl)-4-amino-(2R)-methylbutanoic acid, or a pharmaceutically acceptable salt thereof, to the patient in need of such treatment, wherein the disease is heart failure with preserved ejection fraction (HF-PEF), and wherein the treatment or delay of progression is characterized by the reduction of the left atrial volume, the left atrial volume index (LAVI) and/or the left atrial dimension.

2. The method according to claim 1, wherein the method is for the treatment of atrial fibrillation or for delaying the time until new onset of atrial fibrillation.

3. The method according to claim 1, wherein the method is for the treatment of patients with no history of atrial fibrillation.

4. The method according to claim 1, wherein the method is for the use of reducing the level of plasma NT-proBNP.

5. The method according to claim 1, wherein the administration of the NEP inhibitor pro-drug or NEP inhibitor leads to a sustained reduction in plasma NT-proBNP concentration.

6. The method according to claim 1, wherein the method is for the improvement, stabilization or delayed worsening in NYHA classification of patients suffering from heart failure.

7. The method according to claim 1, wherein the NEP inhibitor or NEP inhibitor pro-drug is administered together, concomitantly or sequentially with the Angiotensin Receptor Blocker valsartan or a pharmaceutically acceptable salt thereof.

8. The method according to claim 7, wherein the NEP inhibitor or NEP inhibitor pro-drug and the Angiotensin Receptor Blocker are administered in a 1:1 molar ratio.

9. The method according to claim 8 wherein the NEP inhibitor pro-drug delivered by administration of LCZ696 as trisodium[3-((1S,3R)-1-biphenyl-4-ylmethyl-3-ethoxycarbonyl-1-butylcarbamoyl) propionate-(S)-3'-methyl-2'-(pentanoyl{2"-(tetrazol-5-ylate)biphenyl-4'-ylmethyl}amino) butyrate]hemipentahydrate.

10. The method according to claim 9 wherein LCZ696 is administered twice daily at a dose of 50 mg, 100 mg, 200 mg or 400 mg.

* * * * *

UNITED STATES PATENT AND TRADEMARK OFFICE
CERTIFICATE OF CORRECTION

Page 1 of 2

PATENT NO. : 9,517,226 B2
APPLICATION NO. : 14/422855
DATED : December 13, 2016
INVENTOR(S) : Christoph Schumacher et al.

It is certified that error appears in the above-identified patent and that said Letters Patent is hereby corrected as shown below:

In the Specification

Column 2:
Line 37, "provide" should read --provides--;
Line 52, "RAS system" should read --the RAAS system--; and
Line 61, "have showed" should read --have shown--.

Column 3:
Line 4, "to consider" should read --to consideration--;
Line 5, "administer" should read --administration of--; and
Line 8, "providing" should read --provide--.

Column 6:
Line 55, "based" should read --is based--.

Column 8:
Line 59, "is" should read --are--; and
Line 60, "understood" should read --understood to refer to--.

Column 9:
Line 5, "and or" should read --and--.

Column 11:
Line 59, "N-(1-(3-(N-t-butoxycarbonyl-(S)-prolylamino)-2(S)-t-bu-" should read
--N-(1-(3-(N-t-butoxycarbonyl-(S)-propylamino)-2(S)-t-bu- --; and
Line 60, "toxy -carbonylpropylycyclopentanecarbonyl)-O-benzyl-(S)-" should read
--toxycarbonylpropyl)-cyclopentanecarbonyl)-O-benzyl-(S)- --.

Signed and Sealed this
Eighth Day of February, 2022

Drew Hirshfeld
*Performing the Functions and Duties of the
Under Secretary of Commerce for Intellectual Property and
Director of the United States Patent and Trademark Office*

Column 12:
Line 24, "methylphenyl)propioyl]-methionine,    N-[2(S)-" should read --methylphenyl)propionyl]-methionine, N-[2(S)- --.

Column 14:
Line 3, "which are" should read --who have--; and
Line 7, "pharmaceutical" should read --pharmaceutically--.

Column 16:
Line 56, "thereof,—" should read --thereof— --.

Column 17:
Line 27, "which are" should read --who have--.

Column 20:
Line 22, "angiotension" should read --angiotensin--.

Column 24:
Line 65, "Investigator's" should read --investigator's--.

Column 26:
Line 8, "830.6 µg/mL" should read --830.6 pg/mL--.